US012354716B2

(12) United States Patent
Bixon et al.

(10) Patent No.: US 12,354,716 B2
(45) Date of Patent: *Jul. 8, 2025

(54) HANDLING AND TRACKING OF BIOLOGICAL SPECIMENS FOR CRYOGENIC STORAGE

(71) Applicant: TMRW Life Sciences, Inc., New York, NY (US)

(72) Inventors: Brian Bixon, Jersey City, NJ (US); Kathryn Go, Somerville, MA (US); Amit Gupta, Jersey City, NJ (US); Benjamin Harlow, Brooklyn, NY (US); Alan Murray, New York, NY (US); Tim Sharp, Farmingdale, NY (US)

(73) Assignee: TMRW LIFE SCIENCES, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/487,878

(22) Filed: Oct. 16, 2023

(65) Prior Publication Data

US 2024/0120040 A1    Apr. 11, 2024

Related U.S. Application Data

(63) Continuation of application No. 17/321,174, filed on May 14, 2021, now Pat. No. 11,817,187.
(Continued)

(51) Int. Cl.
*G16H 10/40* (2018.01)
*A01N 1/144* (2025.01)
(Continued)

(52) U.S. Cl.
CPC ............. *G16H 10/40* (2018.01); *A01N 1/144* (2025.01); *G06K 7/1413* (2013.01);
(Continued)

(58) Field of Classification Search
CPC ....... A01N 1/0252; G16H 70/20; G16H 70/60
(Continued)

(56) References Cited

U.S. PATENT DOCUMENTS 4,573,581 A    3/1986 Galloway et al.
D300,583 S    4/1989 Smith
(Continued)

FOREIGN PATENT DOCUMENTS

AU    2011357590 B2    9/2015
AU    2017287017 A1    1/2019
(Continued)

OTHER PUBLICATIONS

Comiso, S. et al.; Biot cryocarrier-standardized cryogenic temperature handling of biospecimens; Biopreservation and Biobanking 13.3: A15. Mary Ann Liebert Inc. (Jun. 2015) (Year: 2015).*
(Continued)

*Primary Examiner* — Hiep V Nguyen
(74) *Attorney, Agent, or Firm* — Cozen O'Connor

(57) ABSTRACT

A biological specimen of a subject is handled and tracked for a procedure involving that specimen. Prior to initiation of the procedure, a first procedure data structure (PDS) is generated. The first PDS binds an identifier corresponding to the subject with an indicator of a procedure to be performed on the specimen and identifiers of a specimen container and a specimen holder that physically contacts the biological specimen, as well as a scheduled time for the procedure. A schedule of a plurality of PDSs including the first PDS, is displayed on a display device of a graphical user interface. Following initiation of the procedure, the first PDS is updated based on user input, and after the procedure, at least a portion of the first PDS, as updated, is stored in a database in conjunction with other PDSs respectively associated with other completed procedures.

26 Claims, 18 Drawing Sheets

Related U.S. Application Data

(60) Provisional application No. 63/026,526, filed on May 18, 2020.

(51) Int. Cl.
*G06K 7/14* (2006.01)
*G16H 40/20* (2018.01)
*G16H 40/67* (2018.01)
*G16H 70/20* (2018.01)
*G16H 70/60* (2018.01)

(52) U.S. Cl.
CPC ........... *G06K 7/1417* (2013.01); *G16H 40/20* (2018.01); *G16H 40/67* (2018.01); *G16H 70/20* (2018.01); *G16H 70/60* (2018.01)

(58) Field of Classification Search
USPC .......................................................... 705/2
See application file for complete search history.

(56) References Cited

U.S. PATENT DOCUMENTS

| | | | |
|---|---|---|---|
| D310,264 S | 8/1990 | Leoncavallo et al. | |
| 5,024,830 A * | 6/1991 | Linner .................... | A01N 1/00 435/40.52 |
| 5,176,202 A | 1/1993 | Richard | |
| 5,355,684 A | 10/1994 | Guice | |
| 5,545,562 A | 8/1996 | Cassou et al. | |
| D382,809 S | 8/1997 | Aldrich et al. | |
| D382,810 S | 8/1997 | Aldrich et al. | |
| 5,711,446 A | 1/1998 | Jeffs et al. | |
| 5,741,462 A | 4/1998 | Nova et al. | |
| 5,751,629 A | 5/1998 | Nova et al. | |
| 5,874,214 A | 2/1999 | Nova et al. | |
| D408,145 S | 4/1999 | Au | |
| 5,921,102 A | 7/1999 | Vago | |
| 5,925,562 A | 7/1999 | Nova et al. | |
| 5,964,095 A | 10/1999 | Coelho et al. | |
| 6,066,300 A | 5/2000 | Carey et al. | |
| 6,100,026 A | 8/2000 | Nova et al. | |
| 6,141,975 A | 11/2000 | Tatsumi | |
| 6,156,566 A | 12/2000 | Bryant | |
| 6,302,327 B1 | 10/2001 | Coelho et al. | |
| 6,329,139 B1 | 12/2001 | Nova et al. | |
| 6,564,120 B1 | 5/2003 | Richard et al. | |
| D484,797 S | 1/2004 | Kipperman et al. | |
| 6,701,743 B1 | 3/2004 | Durst et al. | |
| D496,398 S | 9/2004 | Greenberg | |
| 6,888,063 B1 | 5/2005 | Lien et al. | |
| D506,550 S | 6/2005 | Greenberg | |
| 7,070,053 B1 | 7/2006 | Abrams et al. | |
| 7,091,864 B2 | 8/2006 | Veitch et al. | |
| D535,478 S | 1/2007 | Uffner et al. | |
| 7,278,328 B2 | 10/2007 | Massaro | |
| 7,316,896 B2 | 1/2008 | Kuwayama et al. | |
| 7,350,703 B2 | 4/2008 | Ambartsoumian | |
| 7,411,508 B2 | 8/2008 | Harazin et al. | |
| D576,488 S | 9/2008 | Miota et al. | |
| D592,966 S | 5/2009 | Nissen | |
| 7,661,591 B2 | 2/2010 | Dearing et al. | |
| 7,694,886 B2 | 4/2010 | Tan et al. | |
| 7,861,540 B2 | 1/2011 | Cloutier et al. | |
| 7,870,748 B2 | 1/2011 | Byrne | |
| D642,697 S | 8/2011 | Gaefvert | |
| 8,097,199 B2 | 1/2012 | Abbott et al. | |
| 8,098,162 B2 | 1/2012 | Abbott et al. | |
| 8,115,599 B2 | 2/2012 | Harazin et al. | |
| 8,168,138 B2 | 5/2012 | Che et al. | |
| 8,378,827 B2 | 2/2013 | Davidowitz et al. | |
| D682,045 S | 5/2013 | Myoung | |
| 8,502,645 B2 | 8/2013 | Thomas et al. | |
| 8,710,958 B2 | 4/2014 | Yang et al. | |
| 8,790,597 B2 | 7/2014 | Childs et al. | |
| 8,852,536 B2 | 10/2014 | Davidowitz et al. | |
| 8,872,627 B2 | 10/2014 | Davidowitz | |
| 8,884,743 B2 | 11/2014 | Chaffey et al. | |
| 8,919,532 B2 | 12/2014 | Buergermeister et al. | |
| 8,937,550 B2 | 1/2015 | Phaneuf et al. | |
| 9,028,754 B2 | 5/2015 | Winter et al. | |
| 9,033,251 B2 | 5/2015 | Weisshaupt et al. | |
| D733,314 S | 6/2015 | Lui | |
| 9,140,487 B2 | 9/2015 | Chaffey et al. | |
| 9,163,869 B2 | 10/2015 | Warhurst et al. | |
| 9,211,540 B2 | 12/2015 | Lansdowne | |
| 9,280,738 B2 | 3/2016 | Dor et al. | |
| 9,289,770 B2 | 3/2016 | Lavi | |
| 9,297,499 B2 | 3/2016 | Jimenez-Rios et al. | |
| 9,418,265 B2 | 8/2016 | Morris et al. | |
| 9,431,692 B2 | 8/2016 | Davidowitz et al. | |
| D768,868 S | 10/2016 | Inoue | |
| D771,271 S | 11/2016 | Zingre | |
| 9,501,734 B2 | 11/2016 | Morris | |
| 9,516,876 B2 | 12/2016 | Inoue | |
| D777,941 S | 1/2017 | Piramoon | |
| 9,538,746 B2 | 1/2017 | Inoue | |
| 9,538,747 B2 | 1/2017 | Inoue | |
| 9,547,782 B2 | 1/2017 | Lansdowne | |
| 9,551,649 B2 | 1/2017 | Houghton et al. | |
| 9,589,225 B2 | 3/2017 | Morris | |
| 9,619,678 B2 | 4/2017 | Morris et al. | |
| 9,697,457 B2 | 7/2017 | Morris | |
| 9,723,832 B2 | 8/2017 | Camenisch et al. | |
| 9,736,890 B2 | 8/2017 | Chaffey et al. | |
| 9,764,325 B2 | 9/2017 | Davidowitz | |
| 9,796,574 B2 | 10/2017 | Frey et al. | |
| 9,928,457 B2 | 3/2018 | McDowell | |
| D816,165 S | 4/2018 | Haug | |
| D835,472 S | 12/2018 | Seiders et al. | |
| 10,156,386 B2 | 12/2018 | Bartlett et al. | |
| D840,684 S | 2/2019 | Luburic | |
| 10,207,270 B2 | 2/2019 | Lansdowne | |
| 10,241,015 B2 | 3/2019 | Hollabaugh et al. | |
| D845,139 S | 4/2019 | Wilson et al. | |
| 10,328,431 B2 | 6/2019 | Davidowitz | |
| 10,401,082 B2 | 9/2019 | Coradetti et al. | |
| 10,493,457 B2 | 12/2019 | Croquette et al. | |
| 10,531,657 B2 | 1/2020 | Farrington et al. | |
| D874,875 S | 2/2020 | Huang | |
| 10,561,141 B2 | 2/2020 | Suzuki et al. | |
| D881,568 S | 4/2020 | Luburic | |
| 10,677,810 B2 | 6/2020 | Grimwood et al. | |
| D890,948 S | 7/2020 | Figueredo et al. | |
| 10,748,050 B2 | 8/2020 | Morris et al. | |
| D910,836 S | 2/2021 | Sandberg et al. | |
| 10,973,226 B2 | 4/2021 | Blair et al. | |
| 10,989,636 B2 | 4/2021 | Gutelius et al. | |
| D928,343 S | 8/2021 | Bonnoitt et al. | |
| D930,186 S | 9/2021 | Kim | |
| D931,128 S | 9/2021 | Li | |
| D932,906 S | 10/2021 | Schulz | |
| 11,148,143 B2 | 10/2021 | Davidowitz et al. | |
| 11,175,298 B2 | 11/2021 | Neeper et al. | |
| D938,053 S | 12/2021 | Xiao | |
| D945,271 S | 3/2022 | Halgren et al. | |
| D963,194 S | 9/2022 | Bixon et al. | |
| D981,801 S | 3/2023 | Wu | |
| 2002/0190845 A1 | 12/2002 | Moore | |
| 2002/0196146 A1 | 12/2002 | Moore | |
| 2003/0017082 A1 | 1/2003 | Van Deursen et al. | |
| 2003/0174046 A1 | 9/2003 | Abrams | |
| 2004/0100415 A1 | 5/2004 | Veitch et al. | |
| 2005/0058483 A1 | 3/2005 | Chapman et al. | |
| 2005/0237195 A1 | 10/2005 | Urban | |
| 2005/0247782 A1 | 11/2005 | Ambartsoumian | |
| 2006/0051239 A1 | 3/2006 | Massaro | |
| 2006/0283945 A1 | 12/2006 | Excoffier et al. | |
| 2007/0068208 A1 | 3/2007 | Norman et al. | |
| 2007/0172396 A1 | 7/2007 | Neeper et al. | |
| 2008/0012687 A1 | 1/2008 | Rubinstein | |
| 2008/0024301 A1 | 1/2008 | Fritchie et al. | |
| 2008/0121700 A1 | 5/2008 | Dearing et al. | |
| 2008/0239478 A1 | 10/2008 | Tafas et al. | |
| 2009/0015430 A1 | 1/2009 | Harazin et al. | |

(56) References Cited

U.S. PATENT DOCUMENTS

| | | |
|---|---|---|
| 2009/0026907 A1 | 1/2009 | Davidowitz et al. |
| 2009/0188272 A1 | 7/2009 | Cloutier et al. |
| 2009/0318751 A1 | 12/2009 | Lansdowne |
| 2009/0322486 A1 | 12/2009 | Gerstel |
| 2010/0028214 A1 | 2/2010 | Howard et al. |
| 2010/0123551 A1 | 5/2010 | Fritchie |
| 2010/0141384 A1 | 6/2010 | Chen et al. |
| 2010/0281886 A1 | 11/2010 | Shaham et al. |
| 2010/0302040 A1 | 12/2010 | Davidowitz et al. |
| 2010/0318217 A1 | 12/2010 | Ferrer et al. |
| 2011/0088424 A1 | 4/2011 | Cloutier et al. |
| 2011/0088517 A1 | 4/2011 | Tsujimura et al. |
| 2011/0137812 A1 | 6/2011 | Sherga |
| 2011/0143452 A1 | 6/2011 | Che et al. |
| 2011/0181875 A1 | 7/2011 | Nakahana et al. |
| 2011/0199187 A1 | 8/2011 | Davidowitz |
| 2011/0199188 A1 | 8/2011 | Dickson |
| 2011/0308271 A1 | 12/2011 | Schryver |
| 2011/0312102 A1 | 12/2011 | Jo |
| 2012/0060514 A1 | 3/2012 | Warhurst et al. |
| 2012/0060520 A1 | 3/2012 | Collins et al. |
| 2012/0060539 A1 | 3/2012 | Hunt et al. |
| 2012/0060541 A1 | 3/2012 | Hunt et al. |
| 2012/0064603 A1 | 3/2012 | Childs et al. |
| 2012/0167786 A1* | 7/2012 | Laugharn, Jr. ......... G01N 1/286 73/864.91 |
| 2012/0187197 A1 | 7/2012 | Masin |
| 2012/0256806 A1 | 10/2012 | Davidowitz et al. |
| 2012/0272500 A1 | 11/2012 | Reuteler |
| 2012/0293338 A1 | 11/2012 | Chaffey et al. |
| 2013/0011226 A1 | 1/2013 | Camenisch et al. |
| 2013/0048711 A1 | 2/2013 | Burns et al. |
| 2013/0076215 A1 | 3/2013 | Davidowitz et al. |
| 2013/0106579 A1 | 5/2013 | Aubert et al. |
| 2013/0119562 A1 | 5/2013 | Shimizu et al. |
| 2013/0151004 A1 | 6/2013 | Winter et al. |
| 2013/0152710 A1 | 6/2013 | Laugharn et al. |
| 2013/0217107 A1 | 8/2013 | Pederson et al. |
| 2013/0342320 A1 | 12/2013 | Hinman et al. |
| 2014/0008355 A1 | 1/2014 | Chaffey et al. |
| 2014/0157798 A1 | 6/2014 | Jimenez-Rios et al. |
| 2014/0171829 A1 | 6/2014 | Holmes et al. |
| 2014/0230472 A1 | 8/2014 | Coradetti et al. |
| 2014/0352456 A1 | 12/2014 | Davidowitz |
| 2015/0045782 A1 | 2/2015 | Ottanelli |
| 2015/0084771 A1 | 3/2015 | Nikitin et al. |
| 2015/0122887 A1 | 5/2015 | Morris et al. |
| 2015/0125574 A1 | 5/2015 | Arent et al. |
| 2015/0153369 A1 | 6/2015 | Giovanoli |
| 2015/0204598 A1 | 7/2015 | Affleck et al. |
| 2015/0205986 A1 | 7/2015 | Morris et al. |
| 2015/0273468 A1 | 10/2015 | Croquette et al. |
| 2015/0295328 A1 | 10/2015 | Fireaizen |
| 2015/0356398 A1 | 12/2015 | Morris |
| 2015/0379390 A1 | 12/2015 | Morris |
| 2016/0026911 A1 | 1/2016 | Morris et al. |
| 2016/0063287 A1 | 3/2016 | Birrer et al. |
| 2016/0085913 A1* | 3/2016 | Evans .................... G16H 30/00 705/3 |
| 2016/0086003 A1 | 3/2016 | Nikitin |
| 2016/0095309 A1 | 4/2016 | Reuteler |
| 2016/0101908 A1 | 4/2016 | Minnette et al. |
| 2016/0143270 A1 | 5/2016 | Schryver |
| 2016/0175837 A1 | 6/2016 | Chaffey et al. |
| 2016/0236387 A1 | 8/2016 | Carroll et al. |
| 2016/0288999 A1 | 10/2016 | Caveney et al. |
| 2016/0289000 A1 | 10/2016 | Caveney et al. |
| 2016/0349172 A1 | 12/2016 | Houghton et al. |
| 2016/0353730 A1 | 12/2016 | Harston et al. |
| 2016/0358062 A1 | 12/2016 | Morris |
| 2017/0113909 A1 | 4/2017 | Frey et al. |
| 2017/0122846 A1 | 5/2017 | Holmes et al. |
| 2017/0184479 A1 | 6/2017 | Schryver et al. |
| 2017/0190056 A1 | 7/2017 | Lapham et al. |
| 2017/0320054 A1 | 11/2017 | Crum et al. |
| 2018/0020659 A1 | 1/2018 | Camenisch et al. |
| 2018/0043364 A1 | 2/2018 | Davidowitz |
| 2018/0055042 A1 | 3/2018 | Sarmentero Ortiz |
| 2018/0086533 A1 | 3/2018 | Kjelland |
| 2018/0100868 A1 | 4/2018 | Grimwood et al. |
| 2018/0128210 A1 | 5/2018 | Garner |
| 2018/0135806 A1 | 5/2018 | Qu et al. |
| 2018/0137315 A1 | 5/2018 | Johns et al. |
| 2018/0154359 A1 | 6/2018 | Ueyama |
| 2018/0202908 A1 | 7/2018 | Croquette et al. |
| 2018/0313498 A1 | 11/2018 | Antola et al. |
| 2018/0368394 A1 | 12/2018 | Kjelland et al. |
| 2019/0000073 A1 | 1/2019 | Pedersen et al. |
| 2019/0025280 A1 | 1/2019 | Kaditz et al. |
| 2019/0060892 A1 | 2/2019 | Davidowitz et al. |
| 2019/0092555 A1 | 3/2019 | Ma et al. |
| 2019/0162639 A1 | 5/2019 | Gutelius et al. |
| 2019/0193078 A1 | 6/2019 | Fiondella et al. |
| 2019/0250181 A1 | 8/2019 | Seeber |
| 2019/0276233 A1 | 9/2019 | Caveney et al. |
| 2019/0293344 A1 | 9/2019 | Sun et al. |
| 2019/0297877 A1 | 10/2019 | Komatsu et al. |
| 2020/0093122 A1 | 3/2020 | Lin et al. |
| 2020/0097788 A1 | 3/2020 | Pedersen et al. |
| 2020/0107541 A1 | 4/2020 | Blair et al. |
| 2020/0143930 A1 | 5/2020 | Catchings et al. |
| 2020/0229431 A1 | 7/2020 | Blair et al. |
| 2020/0248638 A1 | 8/2020 | Engfehr et al. |
| 2020/0281191 A1 | 9/2020 | Ally et al. |
| 2020/0319625 A1 | 10/2020 | Morris et al. |
| 2021/0039937 A1 | 2/2021 | Tansey et al. |
| 2021/0121876 A1 | 4/2021 | Blair et al. |
| 2021/0135061 A1 | 5/2021 | Navabi |
| 2021/0244018 A1 | 8/2021 | Sandy et al. |
| 2022/0087253 A1 | 3/2022 | Gupta et al. |
| 2022/0136656 A1 | 5/2022 | Clarke et al. |
| 2022/0192182 A1 | 6/2022 | Bixon et al. |
| 2022/0221476 A1 | 7/2022 | Craven et al. |
| 2023/0329230 A1 | 10/2023 | Li et al. |

FOREIGN PATENT DOCUMENTS

| | | |
|---|---|---|
| CA | 2972315 A1 | 8/2016 |
| CN | 105857932 A | 8/2016 |
| CN | 105890965 A | 8/2016 |
| CN | 106102460 A | 11/2016 |
| CN | 205815766 U | 12/2016 |
| CN | 106370879 A | 2/2017 |
| CN | 106871546 A | 6/2017 |
| CN | 107624751 A | 1/2018 |
| CN | 108112576 A | 6/2018 |
| CN | 207595583 U | 7/2018 |
| CN | 207663251 U | 7/2018 |
| CN | 207675193 U | 7/2018 |
| CN | 108541702 A | 9/2018 |
| CN | 109258627 A | 1/2019 |
| CN | 208425434 U | 1/2019 |
| CN | 109922887 A | 6/2019 |
| CN | 110476952 A | 11/2019 |
| CN | 110517737 A | 11/2019 |
| CN | 110550327 A | 12/2019 |
| CN | 110583618 A | 12/2019 |
| CN | 110589332 A | 12/2019 |
| CN | 110645752 A | 1/2020 |
| CN | 110667986 A | 1/2020 |
| CN | 210614415 U | 5/2020 |
| CN | 210709605 U | 6/2020 |
| CN | 210709624 U | 6/2020 |
| CN | 210711515 U | 6/2020 |
| CN | 111771211 A | 10/2020 |
| CN | 112090469 A | 12/2020 |
| CN | 112189657 A | 1/2021 |
| CN | 112325976 A | 2/2021 |
| CN | 112325978 A | 2/2021 |
| CN | 112340334 A | 2/2021 |
| CN | 112841172 A | 5/2021 |
| CN | 213274464 U | 5/2021 |
| CN | 112894791 A | 6/2021 |
| CN | 213863260 U | 8/2021 |

(56) References Cited

FOREIGN PATENT DOCUMENTS

| | | |
|---|---|---|
| CN | 213863569 U | 8/2021 |
| CN | 213872207 U | 8/2021 |
| CN | 213874569 U | 8/2021 |
| CN | 213995979 U | 8/2021 |
| CN | 214006820 U | 8/2021 |
| CN | 214216855 U | 9/2021 |
| CN | 214358041 U | 10/2021 |
| CN | 214398091 U | 10/2021 |
| CN | 214758843 U | 11/2021 |
| CN | 115352743 A | 11/2022 |
| CN | 219596677 U | 8/2023 |
| DE | 102011012887 A1 | 8/2012 |
| EP | 0411224 A2 | 2/1991 |
| EP | 0706825 A1 | 4/1996 |
| EP | 0811140 A1 | 12/1997 |
| EP | 1002211 A2 | 5/2000 |
| EP | 1366998 A3 | 3/2004 |
| EP | 1366998 B1 | 1/2006 |
| EP | 1916492 A1 | 4/2008 |
| EP | 2301857 A1 | 3/2011 |
| EP | 2315163 A1 | 4/2011 |
| EP | 2358196 A1 | 8/2011 |
| EP | 2467465 A1 | 6/2012 |
| EP | 2124171 B1 | 8/2012 |
| EP | 2666694 B1 | 7/2014 |
| EP | 1888239 B1 | 10/2014 |
| EP | 1981692 B1 | 6/2015 |
| EP | 2498968 B1 | 9/2015 |
| EP | 2335182 B1 | 10/2015 |
| EP | 2297736 B1 | 2/2016 |
| EP | 2292332 B1 | 7/2016 |
| EP | 2765183 B1 | 7/2016 |
| EP | 2614320 B1 | 10/2016 |
| EP | 2354729 B1 | 12/2016 |
| EP | 2873497 B1 | 5/2017 |
| EP | 2948247 B1 | 11/2017 |
| EP | 2743865 B1 | 6/2019 |
| EP | 2866938 B1 | 6/2019 |
| EP | 2232175 B1 | 8/2019 |
| EP | 3539899 A1 | 9/2019 |
| EP | 2965266 B1 | 10/2019 |
| EP | 2492663 B1 | 12/2019 |
| EP | 3655892 A1 | 5/2020 |
| EP | 3228191 B1 | 8/2020 |
| EP | 4252009 A4 | 4/2024 |
| ES | 2467465 A2 | 6/2014 |
| ES | 2595984 T3 | 1/2017 |
| JP | 2000137031 A | 5/2000 |
| JP | 2001142861 A | 5/2001 |
| JP | 2004028595 A | 1/2004 |
| JP | 2005009863 A | 1/2005 |
| JP | 2005239366 A | 9/2005 |
| JP | 2005321935 A | 11/2005 |
| JP | 2007235905 A | 9/2007 |
| JP | 2007532867 A | 11/2007 |
| JP | 2008021082 A | 1/2008 |
| JP | 2008522184 A | 6/2008 |
| JP | 2010521725 A | 6/2010 |
| JP | 2012526966 A | 11/2012 |
| JP | 5278978 B2 | 5/2013 |
| JP | 2014174647 A | 9/2014 |
| JP | 2015019244 A | 1/2015 |
| JP | 2015087306 A | 5/2015 |
| JP | 2017508984 A | 3/2017 |
| JP | 2017514499 A | 6/2017 |
| JP | 2017165487 A | 9/2017 |
| JP | 2018511782 A | 4/2018 |
| JP | 6343934 B2 | 6/2018 |
| JP | 2018136246 A | 8/2018 |
| JP | 2018529062 A | 10/2018 |
| JP | 2019505042 A | 2/2019 |
| JP | 2019518974 A | 7/2019 |
| JP | 2019529938 A | 10/2019 |
| JP | 2019536973 A | 12/2019 |
| KR | 20080070015 A | 7/2008 |
| KR | 102368093 B1 | 2/2022 |
| WO | 9216800 A1 | 10/1992 |
| WO | 0105687 A1 | 1/2001 |
| WO | 0194016 A1 | 12/2001 |
| WO | 02081743 A2 | 10/2002 |
| WO | 03061381 A1 | 7/2003 |
| WO | 2004026661 A1 | 4/2004 |
| WO | 2005093641 A1 | 10/2005 |
| WO | 2005109332 A1 | 11/2005 |
| WO | 2005115621 A1 | 12/2005 |
| WO | 2006029110 A1 | 3/2006 |
| WO | 2007024540 A1 | 3/2007 |
| WO | 2007049039 A1 | 5/2007 |
| WO | 2007075253 A2 | 7/2007 |
| WO | 2007092119 A1 | 8/2007 |
| WO | 2008024471 A2 | 2/2008 |
| WO | 2008057150 A1 | 5/2008 |
| WO | 2009004366 A1 | 1/2009 |
| WO | 2009017558 A1 | 2/2009 |
| WO | 2009094071 A3 | 10/2009 |
| WO | 2009120596 A1 | 10/2009 |
| WO | 2009155638 A1 | 12/2009 |
| WO | 2010037166 A1 | 4/2010 |
| WO | 2011069190 A1 | 6/2011 |
| WO | 2012083396 A1 | 6/2012 |
| WO | 2012100281 A1 | 8/2012 |
| WO | 2012033605 A3 | 11/2012 |
| WO | 2012033994 A3 | 12/2012 |
| WO | 2012033992 A3 | 4/2013 |
| WO | 2013053011 A1 | 4/2013 |
| WO | 2010014656 A3 | 5/2013 |
| WO | 2012034037 A3 | 5/2013 |
| WO | 2014001819 A1 | 1/2014 |
| WO | 2014006417 A1 | 1/2014 |
| WO | 2014009729 A1 | 1/2014 |
| WO | 2014114938 A2 | 7/2014 |
| WO | 2014135890 A1 | 9/2014 |
| WO | 2014157798 A1 | 10/2014 |
| WO | 2014191757 A1 | 12/2014 |
| WO | 2015073964 A1 | 5/2015 |
| WO | 2015109315 A3 | 10/2015 |
| WO | 2016081755 A1 | 5/2016 |
| WO | 2016120224 A1 | 8/2016 |
| WO | 2016160984 A1 | 10/2016 |
| WO | 2016160986 A3 | 11/2016 |
| WO | 2016200519 A1 | 12/2016 |
| WO | 2017014999 A1 | 1/2017 |
| WO | 2017075144 A1 | 5/2017 |
| WO | 2017109153 A1 | 6/2017 |
| WO | 2017149468 A1 | 9/2017 |
| WO | 2017215957 A1 | 12/2017 |
| WO | 2018000051 A1 | 1/2018 |
| WO | 2018002287 A1 | 1/2018 |
| WO | WO-2018005129 A1 * | 1/2018 ............... B01L 9/06 |
| WO | 2018025053 A1 | 2/2018 |
| WO | 2018039727 A1 | 3/2018 |
| WO | 2018041516 A1 | 3/2018 |
| WO | 2018097267 A1 | 5/2018 |
| WO | 2018215588 A1 | 11/2018 |
| WO | 2019005450 A1 | 1/2019 |
| WO | 2019182900 A1 | 9/2019 |
| WO | 2020033578 A1 | 2/2020 |
| WO | 2020072945 A1 | 4/2020 |
| WO | 2022155225 A1 | 7/2022 |

OTHER PUBLICATIONS

Thermo Fisher Scientific Introduces System to Double Cryogenic Storage Capacity; M2 Presswire Oct. 27, 2011: NA (Year: 2011).*

Zachman, Michael Joseph; High-Resolution Studies of Intact Solid-Liquid Interfaces and Reactive Materials by Cryogenic Electron Microscopy; Cornell University. ProQuest Dissertations & Theses, 2018. 10845397. (Year: 2018).*

International Search Report and Written Opinion for International Application No. PCT/US2020/057779, Mailed on Jun. 17, 2021, 12 pages.

International Search Report and Written Opinion for PCT/US2020/057764, Mailed Date: Feb. 19, 2021, 14 pages.

(56) References Cited

OTHER PUBLICATIONS

International Search Report and Written Opinion for PCT/US2020/060565, mailed Mar. 8, 2021, 11 pages.
International Search Report and Written Opinion for PCT/US2021/051803, mailed Jan. 12, 2022, 6 pages.
International Search Report and Written Opinion for PCT/US2021/062676, mailed Apr. 1, 2022, 9 pages.
International Search Report and Written Opinion for PCT/US2021/063608, mailed Apr. 12, 2022, 11 pages.
International Search Report and Written Opinion for PCT/US2022/012151, mailed Apr. 29, 2022, 9 pages.
International Search Report and Written Opinion for PCT/US2022/028185, mailed Aug. 26, 2022, 11 pages.
International Search Report and Written Opinion for PCT/US2022/077741, mailed date Feb. 1, 2023, 12 pages.
International Search Report for PCT/US2021/032600, mailed Sep. 3, 2021, 4 pages.
Japanese Office Action for Japanese Patent Application No. 2022-525678, mailed May 29, 2023 (with English Translation) 12 pages.
Japanese Office Action for Japanese Patent Application No. 2022-525678, mailed Oct. 12, 2023 (with English Translation) 12 pages.
Japanese Office Action for JP 2022-569516, mailed Nov. 8, 2023, 6 pages {with English Translation).
Japanese Office Action, dated Jun. 6, 2023, for corresponding Japanese Application No. 2022-525679, 16 pages.
Non Final Office Action for U.S. Appl. No. 17/083,179, mailed Sep. 1, 2022, 8 pages.
Non Final Office Action for U.S. Appl. No. 17/321,174, mailed Nov. 22, 2022, 26 pages.
Non-Final Office Action Issued in U.S. Appl. No. 16/840,270, Mailed Sep. 21, 2021, 58 pages.
Notice of Allowance for U.S. Appl. No. 17/321,174, mailed Jul. 12, 2023, 13 pages.
Notice of Allowance for U.S. Appl. No. 29/847,793, mailed Jul. 27, 2023, 2 pages.
Notice of Allowance mailed Jan. 4, 2022, for "Cryogenic Vial", U.S. Appl. No. 29/748,815, 9 pages.
Notice of Reasons for Refusal for Japanese Patent Application No. 2021-518707, mailed May 11, 2022, 11 pages.
Notice of Reasons for Rejection, issued in corresponding Japanese Application No. 2021-518707, dated May 11, 2022, 5 pages.
Office Action dated Sep. 3, 2020, for U.S. Appl. No. 16/840,718, 46 pages.
OXO Airtight Pet Food Storage POP Container. Online published date unknown. Retrieved on May 24, 2022 from URL: https://www.walmart.com/ip/oxo-pet-food-storage-pop-container/623284606, 1 page.
Rienzi, Laura , et al., Poster Witness "Electronic Witness System makes patients less concerned about biological sample mix-up errors and comfortable with IOVF clinical practice", Genera Center for Reproductive Medicine, Via de Notaris 2b, 00197, Rome, Italy. 2015, 1 page.
Final Office Action Issued in U.S. Appl. No. 18/113,297, mailed Aug. 27, 2024, 54 pages.
Notice of Allowance for U.S. Appl. No. 17/490,274, mailed Jun. 26, 2024, 13 pages.
Notice of Reasons for Refusal. Japanese Application No. 2023-518185, dated Jun. 17, 2024, 8 pages.
"Abeyance Web App / Stay Connected", Jul. 6, Abeyance Cry Solutions—Abeyateck, LLC, 2021, 3 pages.
"IVF Witness System: RI Witness TM ART Management System", Confidence, Efficiency and Trust, IVF Witness System—RI Witness—CooperSurgical Fertility Companies https//fertility.coopersurgical.com/equipment/ri-witness—Apr. 19, 2021, 28 pages.
"IVF Witness System: RI Witness TM ART Management System", CooperSurgical Fertility Company 2021, 24 pages.
"RI Witness—Confidence, Efficiency and Trust", CooperSurgical, Fertility and Genomic Solutions, Order No. WIT_BRO_001_V13_ROW—Oct. 13, 2020, 13 pages.

"RI Witness—Product guide", CooperSurgical Fertility and Genomic Solutions, Order No. EQU_BRO_004, V1: ROW Oct. 24, 2018, 12 pages.
"S840 Lab Mover", Large Volume LNS Dry Vapor Shipper, Products Shipping, Jul. 6, Abeyance Cry Solutions—Abeyateck, LLC, 2021, 3 pages.
"Simple, Secure—190° C LN2 Vapor Storage", Products Shipping, Jul. 6, Abeyance Cry Solutions—Abeyateck, LLC, 2021, 7 pages.
Australian Examination Report mailed Sep. 6, 2023, Application No. 2021276247, 5 pages.
Brady printer Range, "Everyone is Unique" Continual cryopreservation monitoring from RI Witness, CooperSurgical, Inc. Order No. WIT_FLY_010_V2_US Oct. 14, 2020, 3 pages.
Comley, J., "New approaches to sample identification tracking and technologies for maintaining the quality of stored samples," Drug Discovery World Summer 2017, 11 pages.
Coopersurgical, RI Witness, Order No. CE 60010312 Version 3—ROW: Oct. 24, 2018, 12 pages.
Cryogenic Vials, Standard. Online, published date unknown. Retrieved on Dec. 8, 2021 from URL: https://www.nextdayscience.com/cryogenic-vials-standard.htm.
CX100 Cryo Express Dry Shipper With Shipping Case. Online, published date unknown. Retrieved on May 24, 2022 from URL:https://www.mitegen.com/product/cryo-express-dry-shipper-cx100-with-case, 2 pages.
EP Search Report mailed Dec. 5, 2023, in EP App No. 20880407.0, 7 pages.
EP Search Report mailed Nov. 7, 2023, in EP App No. 21808453.1, Nov. 11, 2023.
European Search Report dated Aug. 7, 2023, for European Application No. 19869478.8, 5 pages.
Extended European Search Report dated Jun. 30, 2022, for European Application No. 19869478.8, 9 pages.
FluidX Tri-Coded Jacket: 0.7ml Sample Storage Tube with External Thread; Brooks Life Sciences; https://bioinventory.biostorage.com, 2019, 7 pages.
Fontaine, "Automated Visual Tracking for Behavioral Analysis of Biological Model Organisms," Dissertation (Ph.D.), California Institute of Technology, ProQuest Dissertations Publishing (2008), 156 pages.
HID Beyond Cool: RFID disentangles cryopreservation storage and management, 2015, 4 pages.
Ihmig et al., "Frozen cells and bits," IEEE Pulse, Sep. 2013, 9 pages.
International Preliminary Report on Patentability and Written Opinion from PCT Application No. PCT/GB2005/002048 dated Aug. 23, 2005, 9 pages.
Maggiulli, Roberta, et al., "Implementing an electronic witnessing system into a busy IVF clinic—one clinic's experience", Genera Center for Reproductive Medicine, Rome, Italy, 2 pages.
Swedberg, Claire , "Hitachi Chemical Markets Tiny UHF Tag", https://www.rfidjournal.com/hitachi-chemical-markets-tiny-uhf-tag, Sep. 12, 2010, 4 pages.
Thornhill, A. R, et al., Measuring human error in the IVF laboratory using an electronic witnessing system, Monduzzi Editoriale, Proceedings, 17th World Congress on Controversies in Obstetrics, Genecology & Infertility (GOGI), Nov. 8-11, 2012 Lisbon, Portugal, 6 pages.
Australian Examination Report mailed Feb. 26, 2024, Application No. 2021348066, 8 pages.
Australian Examination Report mailed Mar. 28, 2024, Application No. 2022207973, 4 pages.
EP Search Report mailed Mar. 6, 2024 in EP App No. 22739992.0, 7 pages.
Japanese Office Action, dated Mar. 26, 2024, for corresponding Japanese Application No. 2023-519519, 15 pages.
Non-Final Office Action Issued in U.S. Appl. No. 18/113,297, mailed May 14, 2024, 41 pages.
Notice of Reasons for Refusal. Japanese Application No. 2023-541871, dated Apr. 24, 2024, 3 pages.
Canadian Office Action for Canadian Application No. 3,202,347, dated Nov. 7, 2024, 4 pages.
Chinese Notice of Allowance for Application No. 2023-541871, mailed Oct. 8, 2024, 3 pages.

(56) References Cited

OTHER PUBLICATIONS

Office Action of Canadian Patent Application No. 3,176,037, dated Apr. 30, 2025.

* cited by examiner

Freezing some Oocytes for Danielle Pesina right Now:

please record the details of the Cryodevices in Beacon 1

How Many >> Details

| Cryodevice ID | Count | Type | Screening Status | Maturity | Notes |
|---|---|---|---|---|---|
| 000002430011 | 2 | Oocyte | Unscreened | GV ▷ | |
| 000002430012 | 2 | Oocyte | Unscreened | MI ▷ | |
| 000002430013 | 2 | Oocyte | Unscreened | MII ▷ | |
| 000002430014 | 2 | Oocyte | Unscreened | MII ▷ | |
| 000002430015 | 2 | Oocyte | Unscreened | MII ▷ | |
| 000002430016 | 2 | Oocyte | Unscreened | MII ▷ | |

You're working on Beacon 1 of 2

Benjamin Harlow  ADMIN
TMRW | TMRW NY

FIG. 12

Welcome! You can view, edit, and create new tickets

Benjamin Harlow ADMIN
TMRW | TMRW NY

+ New Ticket

Today

| Date & Time | Patient Name | Identification Number | Date of Birth | Ticket # | Procedure | |
|---|---|---|---|---|---|---|
| 20 APR 2019 09:00 AM | Danielle Pesina | 123-465-789 | 01 MAR 1981 | 648 | FET | |
| 20 APR 2019 09:30 AM | Andrea Morrison | 123-465-789 | 01 MAR 1981 | 643 | Oocytes Freeze | |
| 20 APR 2019 10:00 AM | Amber Flint | 123-465-789 | 01 MAR 1981 | 53 | Oocytes Freeze | |
| 20 APR 2019 10:30 AM | Zoe Rush | 123-465-789 | 01 MAR 1981 | 2971 | Oocytes Freeze | |

Completed

| | | | | | | |
|---|---|---|---|---|---|---|
| 20 APR 2019 09:00 AM | Danielle Pesina | 123-465-789 | 01 MAR 1981 | 648 | FET | |
| 20 APR 2019 09:30 AM | Andrea Morrison | 123-465-789 | 01 MAR 1981 | 643 | Oocytes Freeze | |
| 20 APR 2019 10:00 AM | Amber Flint | 123-465-789 | 01 MAR 1981 | 53 | Oocytes Freeze | |

20 tickets in total, 15 are completed

*FIG. 15*

↵ You're editing the Samples on this Ticket                                    Benjamin Harlow ADMIN
                                                                                              TMRW|TMRW NY ⌜ All Cryodevices are accounted for ⌝                                          In Progress Beacon ID E01628012083766  ⓘ Unscreened                                        4 Cryodevices

| Cryodevice ID | Count | Type | Grade | CyroDate | Biopsy | Results | Notes | Unchanged | Consumed | Discarded |
|---|---|---|---|---|---|---|---|---|---|---|
| 00000243011 | 1 | Embryo | 3-AB | 15 MAR 2018 | Yes | 46xy | Dark | ● | ● | ● |
| 00000243012 | 2 | Embryo | 3-AC | 15 MAR 2018 | No | - |  | ● | ● | ● |
| 00000243013 | 1 | Embryo | 4-BA | 15 MAR 2018 | No | - | Dark | ● | ● | ● |
| 00000243014 | 1 | Embryo | 4-BB | 15 MAR 2018 | No | 46xy |  | ● | ● | ● |

Cancel          ⌞ Update ⌟

*FIG. 16*

← You're viewing Danielle Pesina                                  Benjamin Harlow ADMIN
                                                                          TMRW | TMRW NY Danielle Pesina          123-456-789              01 MAR 1981    Dan.Pesina@email.com Phone Number             Address                                 Patient Consent
123-456-789              144 Street Avenue. Apt 3. Gotham. 10016. New York. USA.    Consented

2 Samples in Inventory

| Cryodevice ID ▾ | Count | Type | Grade | CyroDate | Biopsy | Notes | Screening Status |
|---|---|---|---|---|---|---|---|
| ⊙ ⊙ 00000243011 | 1 | Embryo Day 6 | 3-AA | 10 NOV 2019 | No | Dark | ⓘ Unscreened |
| ⊙ ⊙ 00000243012 | 1 | Embryo Day 6 | 3-AB | 10 NOV 2019 | No |  | ⓘ Unscreened |

Historical Samples

| Cryodevice ID ▾ | Count | Type | Grade | CyroDate | Biopsy | Notes | Screening Status | Status |
|---|---|---|---|---|---|---|---|---|
| ⊙ O 00000243001 | 1 | Embryo Day 6 | 3-AA | 10 NOV 2019 | No | Dark | ⓘ Unscreened | ⊛ Consumed |
| ⊙ O 00000243002 | 1 | Embryo Day 6 | 3-AB | 10 NOV 2019 | No |  | ⓘ Unscreened | ⊛ Discarded |

1 Open Ticket

| Date & Time ▾ | Patient Name | Identification Number | Date of Birth | Peocedure |
|---|---|---|---|---|
| 20 APR 2019 09:00 AM | Danielle Pesina | 123-465-789 | 01 MAR 1981 | FET |

*FIG. 17*

HANDLING AND TRACKING OF BIOLOGICAL SPECIMENS FOR CRYOGENIC STORAGE

PRIOR APPLICATION

This application is a continuation of U.S. patent application Ser. No. 17/321,174 filed May 14, 2021, which claims the benefit of U.S. Provisional Application Ser. No. 63/026,526 filed May 18, 2020, which is incorporated by reference herein.

TECHNICAL FIELD

The present disclosure generally relates to apparatus and methods to facilitate identification and handling of biological specimens such as eggs, sperm, embryos, or other biological tissue, which are stored in cryogenic conditions, as well as planning and tracking the storage, retrieval, and other procedures involving such biological specimens.

BACKGROUND

Long-term preservation of cells and tissues through cryopreservation has broad impacts in multiple fields including tissue engineering, fertility and reproductive medicine, regenerative medicine, stem cells, blood banking, animal strain preservation, clinical sample storage, transplantation medicine, and in vitro drug testing. This can include the process of vitrification in which a biological specimen or sample (e.g., an oocyte, an embryo, a biopsy) contained in or on a storage device (e.g., a cryopreservation straw, cryopreservation tube, stick or spatula) is rapidly cooled by placing the biological specimen and the storage device in a substance, such as liquid nitrogen. This results in a glass-like solidification or glassy state of the biological specimen (e.g., a glass structure at the molecular level), which maintains the absence of intracellular and extracellular ice (e.g., reducing cell damage and/or death) and, upon thawing, improves post-thaw cell viability. To ensure viability, the vitrified biological specimens must then be continuously stored in a liquid nitrogen dewar or other container containing the liquid nitrogen, which is at a temperature of negative 190 degrees Celsius.

There are, however, a number of concerns in how these biological specimens are being stored, identified, managed, inventoried, retrieved, etc. For example, each harvested embryo is loaded on a rigid specimen holder (e.g., embryo straw, stick or spatula). In the case of a tubular specimen holder, the tube may be closed (e.g., plugged) at one end and open at the other end. The specimen holders are used as cryopreservation storage devices to contain or hold the embryos as they are cooled as quickly as possible by plunging the specimen holders with the biological material into a liquid nitrogen bath in a cryogenic freezer at a temperature of approximately negative 190 degrees Celsius, for example to achieve vitrification. Multiple cryopreservation storage devices may be placed in a goblet for placement in the liquid nitrogen storage tank or freezer. The goblet attaches to the liquid nitrogen storage tank such that the multiple cryopreservation storage devices are suspended in the liquid nitrogen. Labels that are manually written-on using a suitable marker pen or printed using a custom printer are attached to the straw and/or the goblet. Such labels can include identification information corresponding to the individual that the embryo was harvested from and other suitable information (e.g., a cryopreservation storage device number, a practitioner number, etc.).

Access to the biological specimens is required from time to time. For example, a particular biological specimen may be retrieved to perform a procedure (e.g., testing of a specimen, in-vitro fertilization, implantation of an embryo in a subject (e.g., subject)). Retrieval of specimen holders and associated biological specimens from the cryogenic refrigerator or cryogenic tank in which the biological specimens are stored exposes the retrieved biological specimens to non-cryogenic conditions (e.g., temperatures above negative 190° C., and depending on a duration of the exposure places the biological specimens at risk. Due to the way biological specimens are stored (e.g., cryopreservation storage devices arrayed in cassettes, cassettes arrayed in stacks), retrieval of one or more desired biological specimens often requires retrieval of additional biological specimens that are not needed at that time, exposing such to risk. In addition, simultaneous handling of multiple biological specimens belonging to different subjects gives rise to the risk of retrieving incorrect biological specimens or misplacing such specimens, which can result in subject-specimen mix-ups, with potentially devastating consequences for subjects and clinics alike.

Solutions are needed to these, and other, challenges to improve the handling and tracking of biological specimens for various procedures involving those specimens.

BRIEF SUMMARY

Accordingly, it is desirable to provide new apparatus and methods for record-keeping and tracking of biological specimens (e.g., eggs, sperm, embryos, other biological tissue) when such specimens are placed into cryogenic storage, or retrieved from cryogenic storage for testing, fertilization, implantation, or other procedure.

Aspects of the disclosure are directed to a method, software, and an apparatus for handling a biological specimen of a subject for a procedure involving that specimen. According to these aspects prior to initiation of the procedure, a first procedure data structure (PDS) to be stored in a non-transitory machine-readable storage medium, is generated. The first PDS binds (a) an identifier corresponding to the subject, (b) an indicator of a procedure to be performed on the biological specimen, wherein the first procedure includes, cryogenic storage or retrieval of the biological specimen, (c) an identifier corresponding to a specimen container of the biological specimen, (d) an identifier corresponding to a specimen holder that physically contacts the biological specimen (e) a scheduled time for the procedure, and (f) an identifier corresponding to the first PDS.

A schedule of a plurality of PDSs including the first PDS, comprising indicia of at least a portion of bindings (a)-(f) for the first PDS, is caused to be displayed, on a display device of a graphical user interface. The procedure associated with the first PDS is initiated based on user input interactive with the displayed schedule. Following initiation of the procedure, the first PDS is updated to indicate (1) an actual time of performance of the procedure, (2) an identification of a human operator carrying out the procedure, and (3) an indication of a condition of the biological specimen as assessed during the procedure. Following conclusion of the procedure, at least a portion of the first PDS, as updated, is stored in a database in conjunction with other PDSs respectively associated with other completed procedures.

BRIEF DESCRIPTION OF THE DRAWINGS

In the drawings, identical reference numbers identify similar elements or acts. The sizes and relativee positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIGS. 10-18 are screen prints of example implementations of a GUI implemented by an example PPTS as it carries out operations in accordance with some embodiments.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with computer systems, actuator systems, and/or communications networks have not been shown or described in detail to avoid unnecessarily obscuring descriptions of the embodiments. In other instances, well-known computer vision methods and techniques for generating perception data and volumetric representations of one or more objects and the like have not been described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
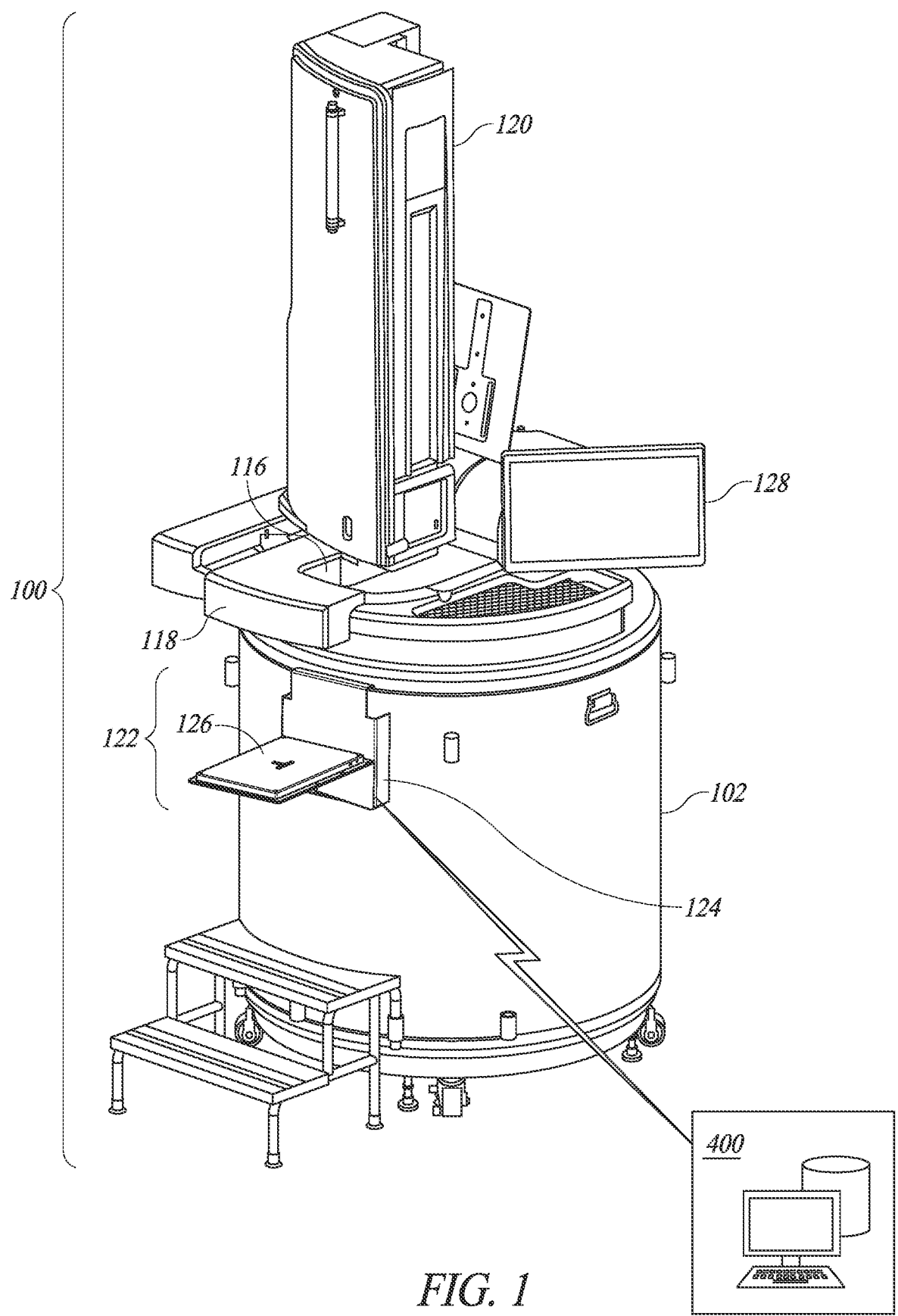
FIG. 1 is an isometric view diagram illustrating a cryogenic storage system interfaced with a procedure planning and tracking system (PPTS) according to at least one illustrated embodiment.

FIG. 1 shows a cryogenic storage system 100 interfaced with a procedure planning and tracking system (PPTS) 400 according to at least one illustrated embodiment. The cryogenic storage system 100 may take may of a large variety of forms, typically including cryogenic storage tank or freezer 102 which can store specimen containers in a cryogenic environment, for example immersed in a bath of liquid nitrogen at a temperature at or below about negative 190° C. The cryogenic storage tank or freezer 102 is typically highly thermally insulated, and may include stainless steel interior and exterior walls with a vacuum or other thermal insulating material therebetween.

Figure 2:
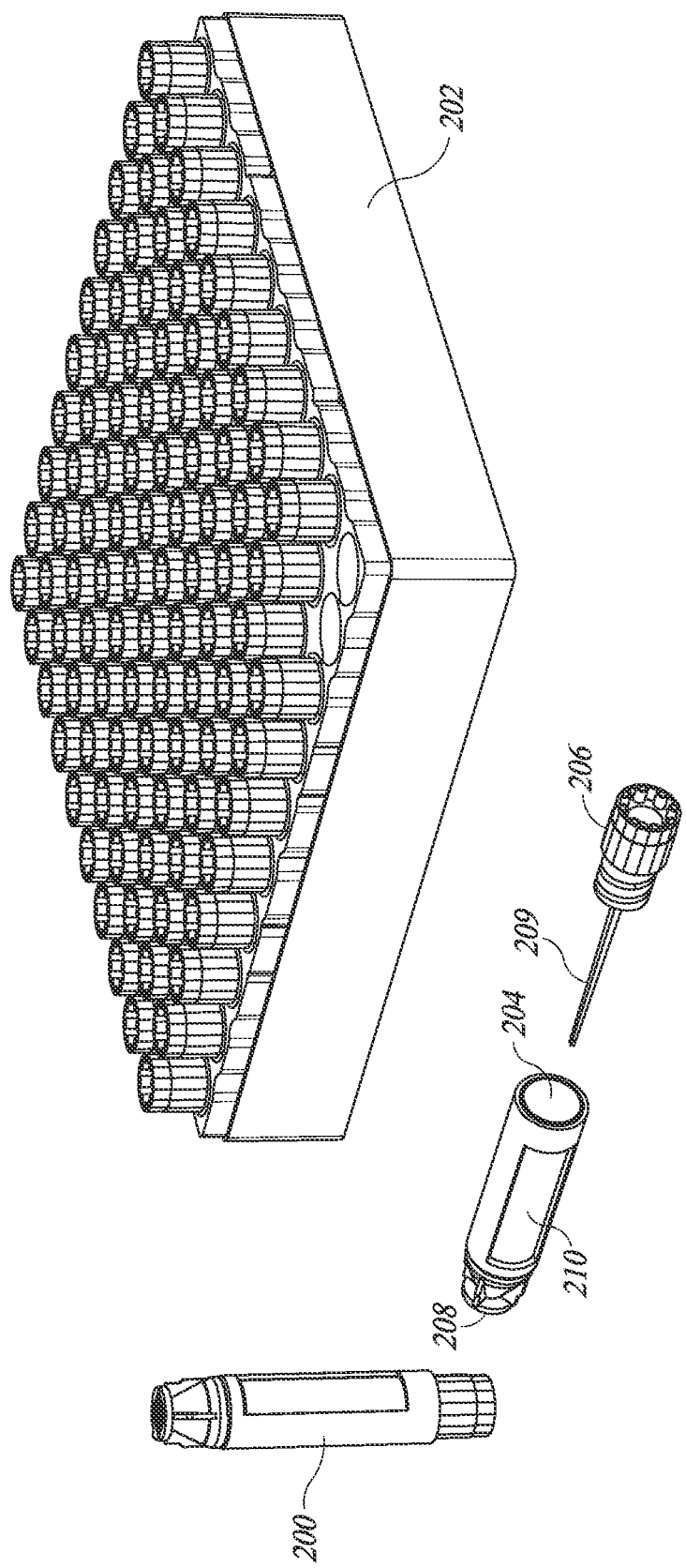
FIG. 2 is an isometric view of a storage cassette holding a plurality of specimen containers, with two of the specimen containers removed from the storage cassette to better illustrate aspects of those storage containers.

As illustrated in FIG. 2, the specimen containers 200 (only one called out) are typically stored in storage cassettes 202 (only one illustrated) for long term storage via a cryogenic refrigerator. Each specimen container 200 may include a vial 204 (only one called out), a cap 206 (only one called out), one or more wireless transponders (e.g., radio frequency identification (RFID) transponders) 208 (only one called out), an elongated specimen holder 209 (e.g., straw, rod, spatula), and optionally one or more machine-readable symbols 210 (only one called out). The specimen containers 200, for example, store specimens of biological tissue, for instance eggs, sperm or embryos. Various implementations of specimen containers are described in U.S. patent application 62/900,281, filed Sep. 13, 2019; U.S. patent application 62/880,786, filed Jul. 31, 2019; U.S. patent application 62/879,160, filed Jul. 26, 2019; U.S. patent application 62/741,986, filed Oct. 5, 2018; and U.S. patent application 62/741,998, filed Oct. 5, 2018.

The specimen containers 200 are typically arrayed in the storage cassette 202, for example arrayed in a two-dimensional array (e.g., 7 by 7, 10 by 10, 8 by 12, 14 by 14). The storage cassettes 202 are typically designed with little thought to use outside of the cryogenic refrigerator since in use, the storage cassettes remain in the cryogenic refrigerator expect for brief periods when removal is needed to retrieve a specimen. Storage cassettes 202 are typically stored in the cryogenic storage tank or freezer 102 in vertical stacks, the vertical stacks also called racks. The stacks or racks of storage cassettes 202 may be annularly arrayed in the cryogenic storage tank or freezer 102 about a central axis of the cryogenic storage tank or freezer 102. The cryogenic storage tank or freezer 102 may include a turntable or convey in the interior thereof, on which the stacks or racks of storage cassettes 202 are carried. This allows respective stacks or racks of storage cassettes 202 to be aligned with an opening 116 of the cryogenic refrigerator for placement or removal.

Returning to FIG. 1, the cryogenic storage tank or freezer 102 includes an opening 116 and a door or cover 118 to selectively open and close the opening 116, to respectively provide access to the interior of the cryogenic storage tank or freezer 102 from an exterior thereof, and to prevent access, as well as hermetically seal the interior from the exterior to maintain the cryogenic temperature in the interior of the cryogenic storage tank or freezer 102. The stacks or racks of storage cassettes 202 may be selectively placed into the interior of the cryogenic storage tank or freezer 102 for storage at cryogenic temperatures and removed from the interior of the cryogenic storage tank or freezer 102 for use via the opening. In some implementations, the stacks or racks of storage cassettes 202 are manually removed from the cryogenic storage tank or freezer 102 when needed, and manually placed in the cryogenic storage tank or freezer 102 to store the specimens in the specimen containers 200 at cryogenic temperatures. In other implementations, the cryogenic storage system 100 includes a picker or elevator 120 to automatically remove selected ones of the stacks or racks of storage cassettes 202 from the cryogenic storage tank or freezer 102 when needed, and to automatically place the storage cassettes 202 with the specimen containers 200 in the cryogenic storage tank or freezer 102 to store the specimens in the specimen containers 200 at cryogenic temperatures. The storage and retrieval mechanism (e.g., turntable, picker or elevator) of the cryogenic storage tank or freezer 102 can automatically replicate movements of a human, and hence is denominated as a robot or robotic system. Whether manually moved or automatically moved, it is typically important to minimize exposure of the specimens to temperatures high than about negative 190° C. (e.g., ambient room temperature or about 23° C.).

A transfer system 122 may facilitate a transfer of specimen containers 200 from the storage cassettes 202 to carrier cassettes or to portable thermally insulated cryogenic carriers in which the carrier cassettes are carried. The transfer system 122 may be part of the cryogenic storage system 100, or may be provided as a separate system that interfaces with the cryogenic storage system 100. For example, the transfer system 122 may interface with a conventional commercially available cryogenic automated storage system (e.g., the Bistore III Cryo −190° C. System sold by Brooks Life Sciences)).

Figure 3:
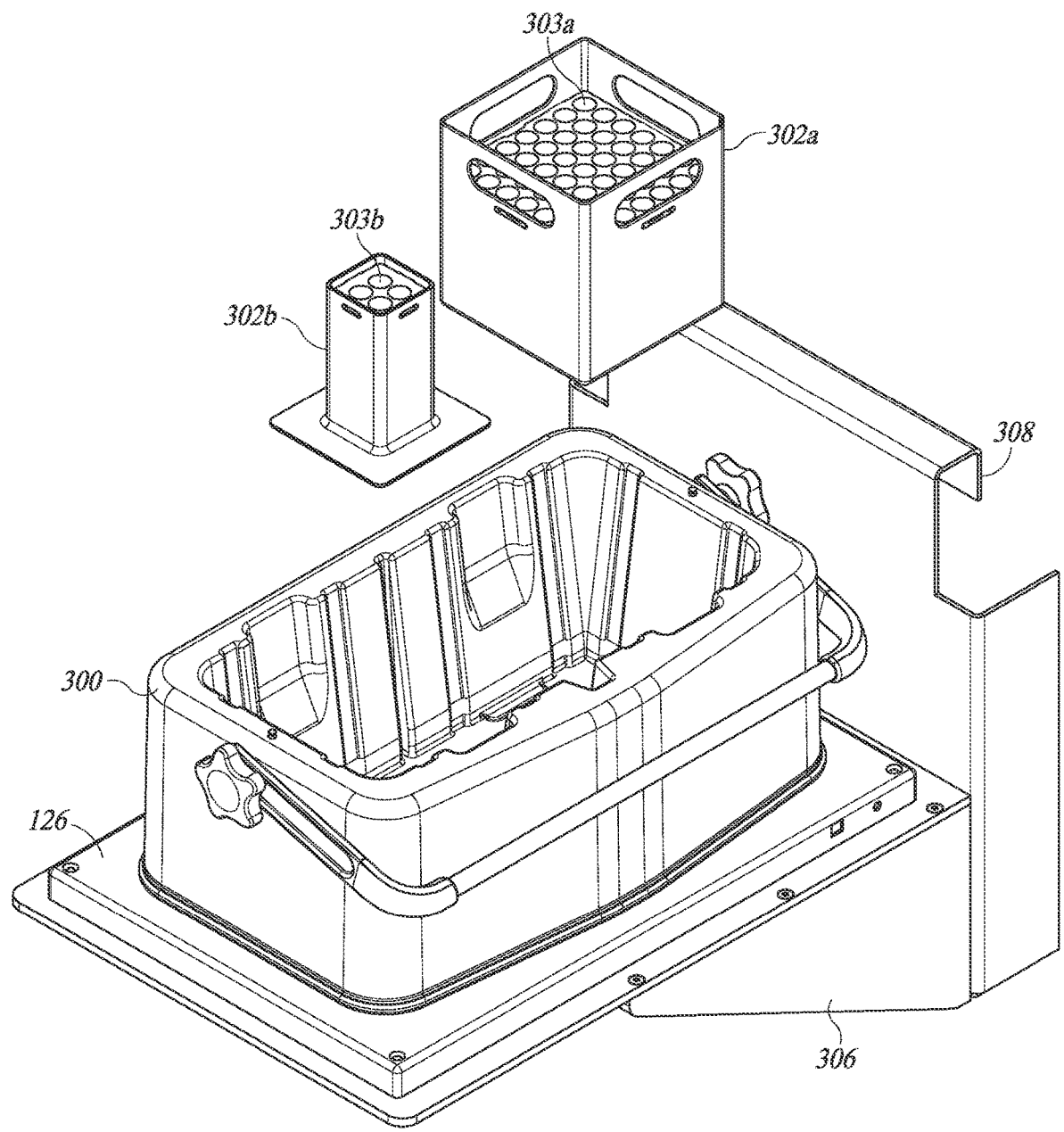
FIG. 3 is an isometric view of a portable thermally insulated cryogenic carrier that carries or holds a number of carrier cassettes positioned with respect to an antenna array of a reader of a transfer system, according to at least one illustrated implementation.

The transfer system 122 includes one or more readers 124 (only one shown in FIG. 1) operable to read information from one or more wireless transponders physically associated with respective specimen containers 200, storage cassettes 202, or carrier cassettes 302 (FIG. 3). The readers 124 may include one or more antennas, for example a two-dimensional array of antennas 126, and one or more transmitters, receivers, transceivers (collectively radios), operable to cause the antennas to emit interrogation signals and to receive response signals in response to the interrogations signals. The reader(s) 124 may take the form of an RFID reader or interrogator. The transfer system 122 may include one or more dedicated user interface components (e.g., touch screen display, speakers, microphones), or may employ a user interface component of the cryogenic storage system 100, for example a touch screen display 128. An example of a transfer system 122 is described in greater detail in U.S. Patent Application No. 62/927,566 filed Oct. 29, 2019.

Portions of the cryogenic system 100 may be of a conventional design. For example, the cryogenic storage tank or freezer or the picker or elevator may take the form of a commercially available automated storage system (e.g., the Bistore III Cryo −190° C. System sold by Brooks Life Sciences). Some, or even all, of the cryogenic system 100 may include structures and methods for described herein, and thus are not known by the applicant to be either conventional or commercially available. For example, the transfer system 122 including the reader 124 is operable to work with a portable thermally insulated cryogenic carrier 300 (FIG. 3, described below), and to facilitate transfer of specimen containers 200 between a storage cassette 202 and carrier cassettes 302a, 302b (FIG. 3, described below, collectively 302) held by the portable thermally insulated cryogenic carrier 300 are not conventional or commercially available. Also for example, the transfer system 122 may include a co-robot 405 to facilitate transfer between storage cassettes 202 retrieved via the picker or elevator 120 and carrier cassettes 302 held by the portable thermally insulated cryogenic carrier 300 are not known by the applicant to be either conventional or commercially available.

FIG. 3 shows a portable thermally insulated cryogenic carrier 300 that carries or holds a number of carrier cassettes 302a, 302b (two illustrated) positioned with respect to an antenna array 126 of the reader 124 of the transfer system 122, according to at least one illustrated implementation.

The portable thermally insulated cryogenic carrier 300 is shown without a cover, and with the carrier cassettes 302a, 302b removed to better illustrate various features. In use, the portable thermally insulated cryogenic carrier 300 would hold a liquid nitrogen bath in the interior thereof, and the carrier cassettes 302a, 302b would be positioned at least partially immersed in the liquid nitrogen bath in the interior of the portable thermally insulated cryogenic carrier 300, with a cover positioned to close the opening at the top of the portable thermally insulated cryogenic carrier 300.

The carrier cassettes 302a, 302b may each include a number of positions 303a, 303b (only one called out for each carrier cassette 302, 302b) to at least partially receive respective specimen containers thereby (e.g., receptacles, holders, wells), which may be laid out in a two-dimensional array. The carrier cassettes 302a, 302b may include certain features to thermally protect biological specimens held on specimen holders, which are located in specimen containers 200, which are in turn held at various positions 304a, 304b (only one called out for each carrier cassette to prevent clutter in the drawing) carrier cassettes 302a, 302b. For example, each carrier cassette 302a, 302b can comprise a thermal shunt, including an thermally conductive block of material (e.g., aluminum) and an aerogel, with or without a plastic sleeve. Suitable carrier cassettes 302a, 302b are described, for example in U.S. patent application 62/900,281, filed Sep. 13, 2019; U.S. patent application 62/880,786, filed Jul. 31, 2019; U.S. patent application 62/879,160, filed Jul. 26, 2019; U.S. patent application 62/741,986, filed Oct. 5, 2018; and U.S. patent application 62/741,998, filed Oct. 5, 2018. The carrier cassettes 302a, 302b are thus different in designed than the storage cassettes 202 (FIG. 2) since the storage cassettes 202 are designed to be stored in the cryogenic storage tank or freezer 102, and thus do not need added features to prolong cryogenic conditions.

The antenna array 126 or the reader 124 may be supported by a platform or frame 306. The platform or frame 306 may have a lip 308 that allows the platform or frame 306 to be hung from a structure (e.g., edge, handle) of the cryogenic storage tank or freezer 102, advantageously allowing the antenna array 126 or the reader 124 to be positioned proximate the cryogenic storage tank or freezer 102 to facilitate transfers between. This also advantageously allows simplified retrofit of the processor-based transfer system 122 to the cryogenic storage tank or freezer 102. Less advantageously, the platform or frame 306 may be secured to the cryogenic storage tank or freezer 102 via other structures, for example fastened there to via fasteners (e.g., bolts, screws, rivets), adhered thereto by adhesive or epoxy, or soldered thereto via a solder joint.

The processor-based transfer system 122 facilitates transfers, whether automated or manual, of specimen containers 200 (FIG. 2) between storage cassettes 202 (FIG. 2) and carrier cassettes 302 (FIG. 3). The storage cassettes 202 are designed for long term storage in cryogenic refrigerators (e.g., tanks or dewars), which are typically large and heavy fixtures. The carrier cassettes 302 are designed for temporary storage, in a format that is portable. Examples of suitable carrier cassettes 302, and of portable thermally insulated cryogenic carriers 300 that carry the carrier cassettes 302 and which can temporarily maintain cryogenic materials at cryogenic temperatures, as wells as specimen containers 200 for use therewith, are described in U.S. patent application 62/900,281, filed Sep. 13, 2019; U.S. patent application 62/880,786, filed Jul. 31, 2019; U.S. patent application 62/879,160, filed Jul. 26, 2019; U.S. patent application 62/741,986, filed Oct. 5, 2018; and U.S. patent application 62/741,998, filed Oct. 5, 2018.

Figure 4:
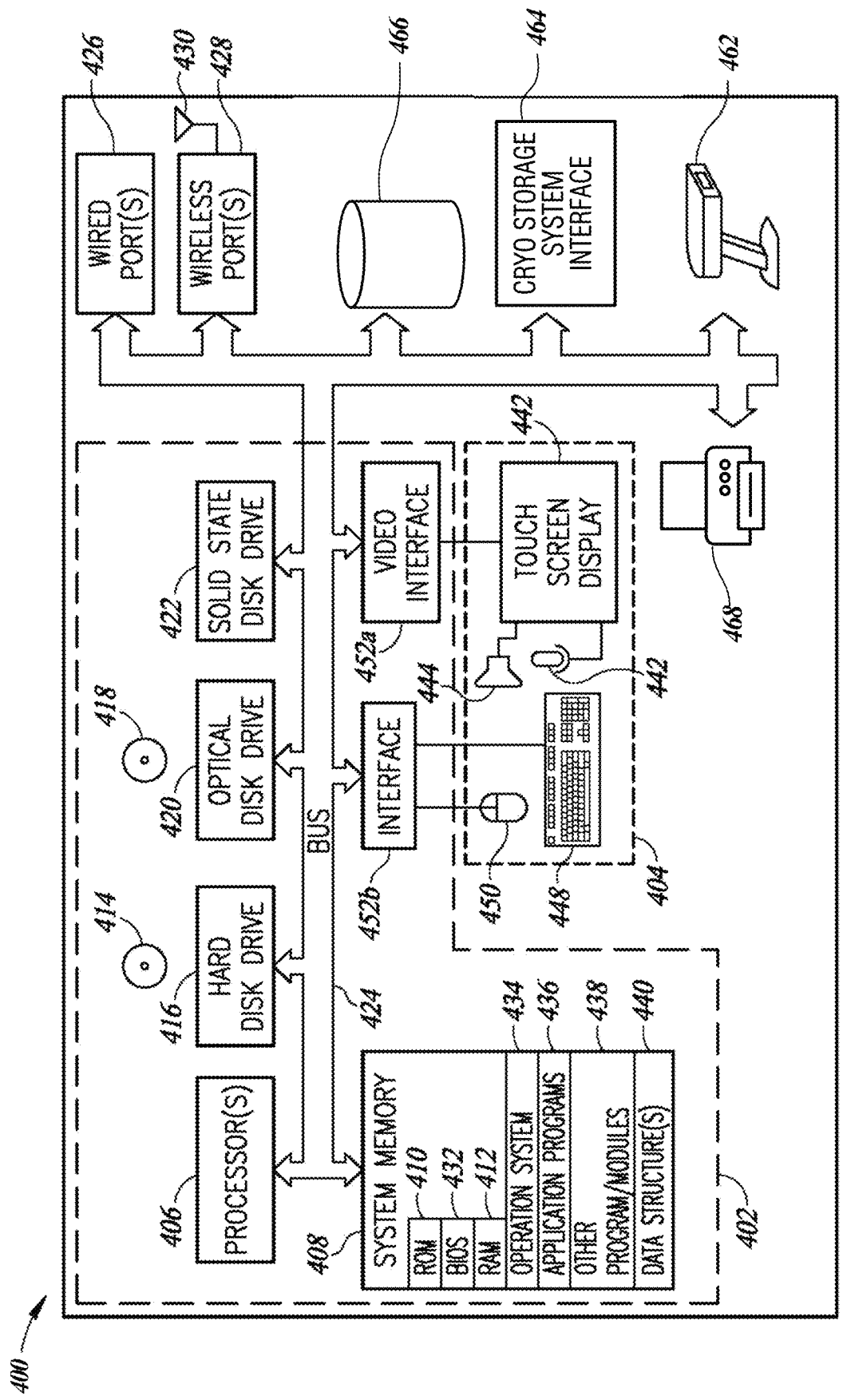
FIG. 4 is a schematic diagram illustrating a PPTS as shown generally in FIG. 1, in greater detail according to some embodiments.

FIG. 4 is a schematic diagram illustrating a PPTS 400 as shown generally in FIG. 1. The PPTS 400 may interface with the processor-based transfer system 122 as depicted, or with a different controller that may be associated with the cryogenic storage system 100.

The processor-based transfer system 122 includes a data-processing subsystem 402, and a user interface system 404. The data-processing subsystem 402 may include one or more processors 406, for example, one or more of: one or more microcontrollers, one or more microprocessors, one or more central processing units, one or more digital signal processors (DSPs), one or more graphics processing units (GPUs), one or more application specific integrated circuits (ASICs), one or more field programmable gate arrays (FPGAs), or one or more programmable logic controllers (PLCs). The data-processing subsystem 402 may include one or more nontransitory storage media, for example, one or more nonvolatile storage media or one or more volatile storage media, for example a system memory 408 that includes one or more of: one or more read only memories (ROMs) 410, one or more random access memories (RAMs) 412, one or more FLASH memory, one or more magnetic disk 414 and associated drives 416, one or more optical disk drives 418 and associated drives 420, one or more solid state drives 422, one or more cache memories, or one or more registers of one or more processors 406. The data-processing subsystem 402 may include one or more communications channels 424 (e.g., buses or system interconnects) that communicatively couple the processor(s) with the storage media. The data-processing subsystem may include one or more communications ports, for example one or more wired communications ports 426, wireless communications ports 428 (e.g., Wi-Fi or Bluetooth radios and associated antennas 430; infrared transceivers) that provide for communications between the data-processing subsystem and external devices.

The processor(s) 406 of the data-processing subsystem 402 are operable to execute logic, for example to execute one or more algorithms stored as processor-executable instructions by the one or more nontransitory storage media. Suitable algorithms are set out herein. Processor-executable instructions may, for example, include a basic input/output operating system (BIOS) 432, for example stored in ROM 410. Processor-executable instructions may, for example, include an operating system (OS) 434, for example stored in RAM 412 during execution. Processor-executable instructions may, for example, include one or more application programs 436, which provide the logic to collect user and subject information, information about biological specimens, planned procedures involving the biological specimens, and the like, which may be stored, for example, in RAM 412 or one or more disk drives 416, 420, 422, or on a remote networked server communicatively coupled via one or more of ports 426, 428 during operation.

In a related type of embodiment, the one or more application programs may include instructions to generate, store, and facilitate user modification of procedure data structures (PDSs). PDSs are data structures that bind an identifier corresponding to the subject, with an indicator of a procedure to be performed on the biological specimen, an identifier corresponding to a specimen container of the biological specimen, an identifier corresponding to a specimen holder, a scheduled time for the procedure; and identifier corresponding to the first PDS. In an example embodiment, when a procedure (such as freezing, or thawing of a specimen for testing, fertilization, implantation, or other operation) is started, the corresponding PDS may be updated to indicate the actual time of performance of the procedure, an identification of the human operator carrying out the procedure, and an indication of a condition of the biological specimen as assessed during the procedure. In other related embodiments, following conclusion of the procedure, at least a portion of the first PDS, as updated, may be stored in a database along with other PDSs corresponding to other completed procedures, from which an audit trail may be generated and displayed.

Processor-executable instructions may include one or more other programs or modules 438, for example to provide for communications with external devices or peripherals, and which may be stored, for example, in RAM 412 during execution. One or more data structures 440 may store information, for example information that identifies specific users, identifies specific clinicians, identifies specific subjects, identifies specific procedures, identifies specific specimen containers and associates the specific specimen containers with specific subjects, and that maps specimen containers to respective storage cassettes or carrier cassettes. The data structures 440 may take a variety of forms including databases, data sets, records and fields, tables, linked lists, trees, binary trees, etc. The data structures 440 may be stored, for example, in RAM 412 during execution.

The processor(s) 406 of the data-processing subsystem are also operable to receive user input from, and provide output to, one or more user interface devices of the user interface system 404, to allow a human user to interact with the PPTS 400.

The user interface system 404 may, for example, include one or more of: one or more display screens, one or more touch-sensitive display screens 442, one or more speakers 444, one or more microphones 446, one or more keyboards 448, one or more pointer devices 450 (e.g., computer mouse, trackpad, trackball), one or more haptic interfaces. The user interfaces 406 are communicatively coupled (e.g., wired, optical, wireless or radio) with the processor(s) via one or more peripheral interfaces to provide user input to the processor(s) 406 and to receive output from the processor(s) 406 to be presented to a user. For instance, the processor(s) 406 may execute processor-executable instructions that cause the processor(s) to cause devices to present a user interface (e.g., a graphical user interface), for instance via a touch screen display 442. Machine-readable symbols, such as one-dimensional or barcode symbols, two-dimensional or matrix code symbols, or other printed symbols (e.g., human-readable symbols), may be read by symbol reader 462. Processor(s) 406 may also be interfaced with a printer 468 for printing labels to be affixed to specimen holders via adhesives that can withstand cryogenic temperatures, or for printing directly on or inscribing in (e.g., laser etching) the specimen holders themselves, in which case processor(s) 406 may execute driver software facilitating use of such printer 468.

The processor(s) 406 may be interfaced with cryogenic storage system 100. Such interface may be implemented via ports 426, 428 or via a cryogenic storage system interface 464, which may utilize a dedicated data-communications controller. Moreover, the processor(s) 406 may be interfaced with a database host system 466, such as a database or file server, or a cloud-storage service, in which PDSs, archives, audit trails, and related data may be primarily stored, backed up, mirrored, or otherwise synchronized.

Figure 5:
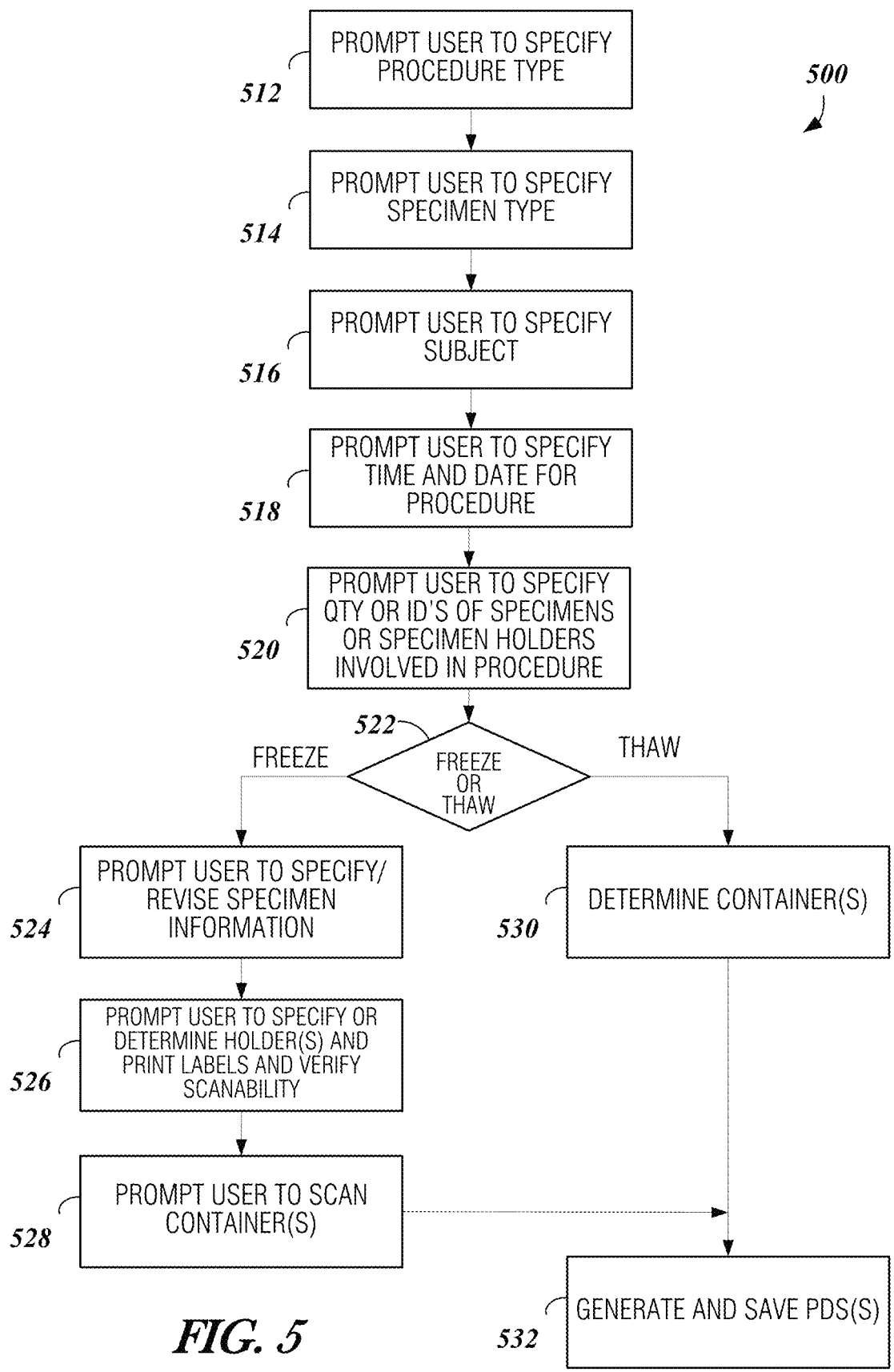
FIG. 5 is a process flow diagram illustrating an example algorithm for facilitating the creation of one or more procedure data structures (PDSs) via user-interactive input, that may be carried out by the PPTS according to some embodiments.

FIG. 5 is a process flow diagram illustrating an example algorithm for facilitating the creation of one or more PDSs via user-interactive input, that may be carried out by PPTS 400 according to some embodiments. Process 500 involves guiding a user, such as a clinician, through a series of interactive prompts to populate the information fields of one or more PDSs. At 512, the user is prompted to specify a procedure type. For instance, the procedure type may be intake of biological specimens for cryogenic preservation (i.e., freezing). Other procedure types may involve retrieval of frozen specimens. For instance, such procedures may include retrieval for testing (e.g., biopsy), retrieval for in-vitro fertilization of an oocyte, or retrieval for frozen-embryo transfer (FET). At 514, the user is prompted to specify the type of specimen to be involved in the procedure. Types of specimens may include sperm, oocytes, embryos, or other biological tissue.

At 516, the user is prompted to specify the subject (i.e., patient) for whom the procedure is being performed. This may involve inputting various items of data about the subject so that verification may be performed to ensure that the subject is the correct subject for the procedure. For instance, the subject's name, birthdate, subject ID, or other information may be entered. In addition, if the subject is present, the subject's photograph or other biometric information may inputted for tracking or verification purposes. If the subject is not present, the subject's photograph or other identifying information may be retrieved from the subject's account for inclusion in the PDS(s).

At 518, the user is prompted to specify the time and date for the procedure. The procedure may be executed promptly, or it may be scheduled for execution in the future. At 520, the user is prompted to specify quantity of identification information about the specimens. For instance, for specimen intake, the user may specify the quantity of specimens or specimen holders to be stored. In cases where one or more specimens are being retrieved, the specific ID(s) of the specimen holder(s) may be entered, or an ID of the specimen container(s) may be entered.

Based on the type of procedure, as determined at decision 522, additional operations are performed. In the case of freezing operations, at 524, the user is prompted to specify or revise details about the specimen. For instance, such details about the specimens, may include the infectiousness condition of the specimens, maturity (e.g., GV, MI, MII), grade, embryo type (e.g., day 1, day 2), whether a biopsy has been taken, and the like. If the specimen is not newly-collected, various items specimen information may be carried over from prior assessments or may be revised as appropriate. At 526, the quantity of specimen holders is specified or automatically determined. For instance, the user may wish to have a certain quantity or maximum quantity of specimens associated with each specimen holder, which can be specified. Separately, the system may determine, based on the supplied quantity information and on specimen type-specific rules, the quantity of specimen holders to be used. In embodiments where specimen holders are not automatically identifiable without human actions, labels may be printed for each specimen holder including a specimen holder identification number, a machine-readable symbol representing the same, the subject's name or other identification, and the date. The user may be prompted to scan the machine-readable symbols to verify that printing was successful.

At 528, the user is prompted to scan one or more specimen container identifiers (e.g., read their RFID tags) to associate those one or more containers with the procedure. At 532, a PDS is generated for each specimen container.

If, at decision 522, it is determined that the operation is a thaw operation, the process branches to 530, where the system determines which specimen container(s) have the desired specimens to be thawed and hence are to be retrieved from cryogenic storage as part of the procedure. Accordingly, at 532 a corresponding PDS is generated for each of those specimen containers.

Figure 6:
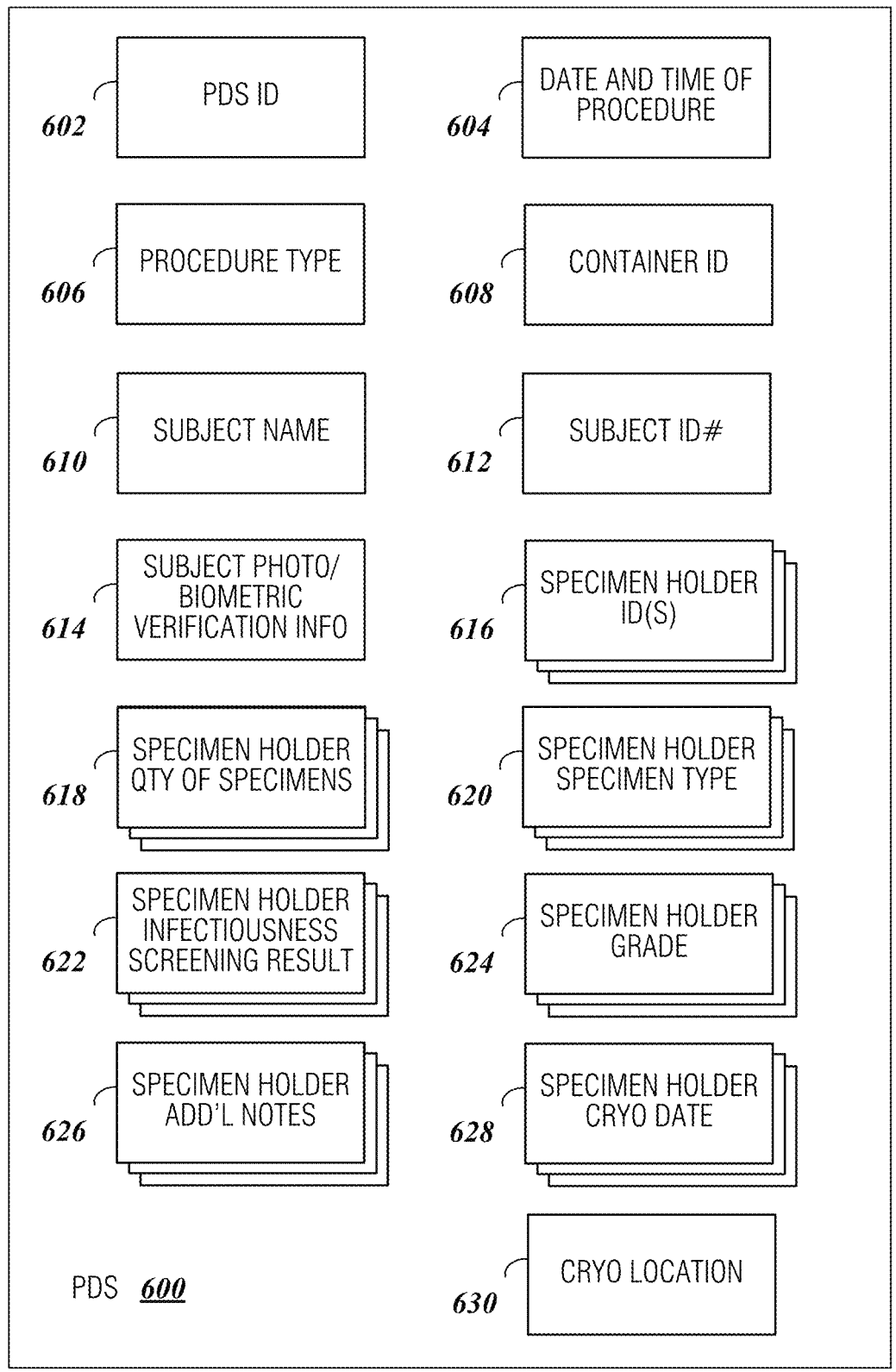
FIG. 6 is a diagram illustrating an example PDS and the various types of information fields that it may contain, according to an embodiment.

FIG. 6 shows an example PDS 600 and the various types of information fields that it may contain. As illustrated, PDS 600 includes a unique PDS ID 602, and the date and time 604 of the procedure, which may indicate a scheduled date and time, an actual date and time when the procedure was performed, or both. In addition, PDS 600 includes the procedure type 606 (freeze, re-freeze, retrieval for procedure A, retrieval for procedure B, etc.). Specimen container ID 608 corresponds to the unique RFID identifier stored and transmitted by the container's RFID tag. In some implementations, the specimen container ID 608 may be different from the unique RFID identifier stored and transmitted by container's RFID tag. In such implementations, a data structure stored on a nontransitory processor-readable medium may store a mapping between the specimen container IDs 608 and the unique RFID identifiers of the RFID tags. In some embodiments, there is a one-to-one correspondence between PDS 600 and the specimen container with which it is associated. PDS 600 includes subject-specific information such as subject name 610, subject ID number 612, and subject verification information such as a photograph, or biometric information (e.g., a cryptographic hash of the subject's iris scan data, fingerprint, etc.).

Other fields pertain to details of the specimens. As discussed above, a specimen container may contain a set of specimen holders. Accordingly, each specimen holder is identified by its ID 616. For each specimen holder ID, specific information may be included, such as the quantity of specimens in that specimen holder 618, the type of specimen in each specimen holder 620 (e.g., embryo, day 6), the per-embryo-holder infection screening result 622, the per-embryo-holder grading of specimen 624 (e.g., 3-AB 3-AC), additional notes 626, and the date of cryogenic storage 628 for each respective specimen holder.

In some embodiments, the location within the cryogenic chamber 630 may be included, such as the vessel, rack, shelf, cassette ID, and intra-cassette location. One function of PDS 600 is to bind all of these fields to one another. Therefore, each PDS 600 is a record representing a future, current, or past procedure, associated with a specific subject, and specific specimens of a specific specimen container. In a related embodiment, a collection of PDSs that are stored in PPTS 400 may be arranged to schedule the operations of a particular cryogenic/fertility services clinic. Likewise, each PPTS may be utilized as a "live record" of each procedure, along with the initial or resulting state of the specimen(s) before and after the procedure, respectively. Additionally, the information stored in completed PPTSs may be gathered to produce an audit trail of the procedures, information about their execution, and their results for each subject, or for a given subject's individual specimen holder ID(s), for example.

Figure 7:
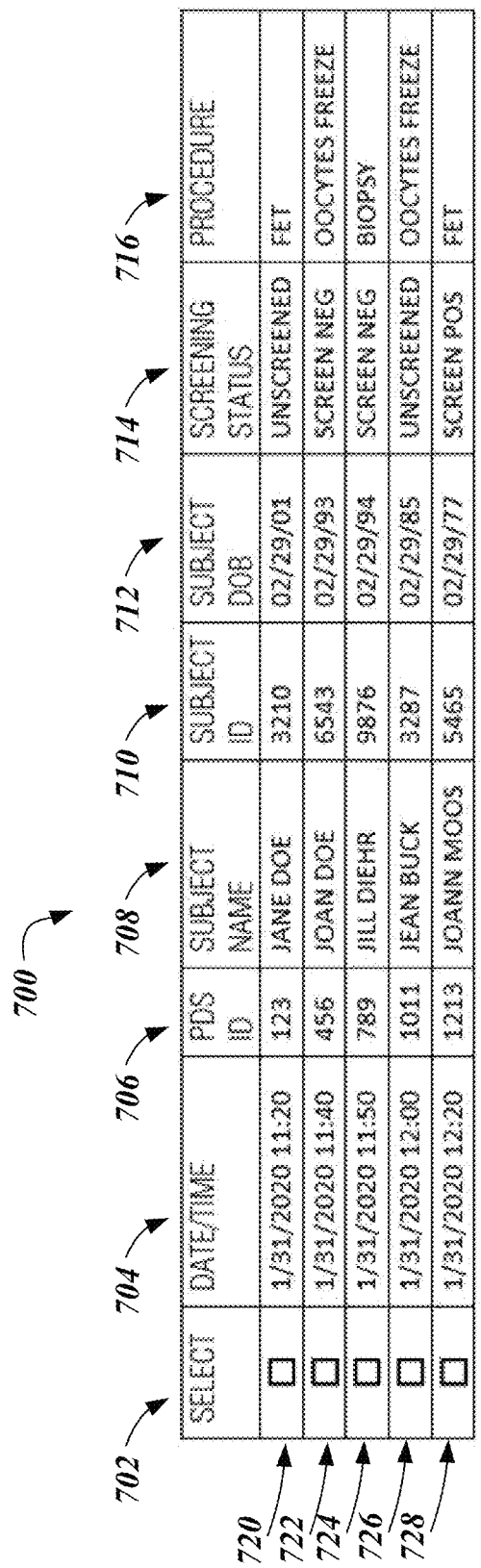
FIG. 7 is a diagram illustrating an example of a schedule display showing a plurality of selectable PDSs.

FIG. 7 shows an example of a schedule display 700 including a plurality of selectable PDSs 720-722. Schedule display 700 may be presented to a clinician who is a user of a PPTS 400. Each row of schedule display 700 corresponds to an individual PDS. For purposes of illustrating schedule 700, in this embodiment, only a portion of the fields of each PDS are shown. In this example, column 702 includes a selection control with which a user may select a given PDS to execute, view in greater detail, modify, or delete. The fields shown include the scheduled date and time 704 of execution, the unique ID 706 of each respective PDS, the name, ID, and date of birth of each respective subject are shown in columns 708-712. Likewise, the infectiousness screening status and result is shown in column 714. Column 716 identifies the procedure type of each PDS 720-728.

Figure 8:
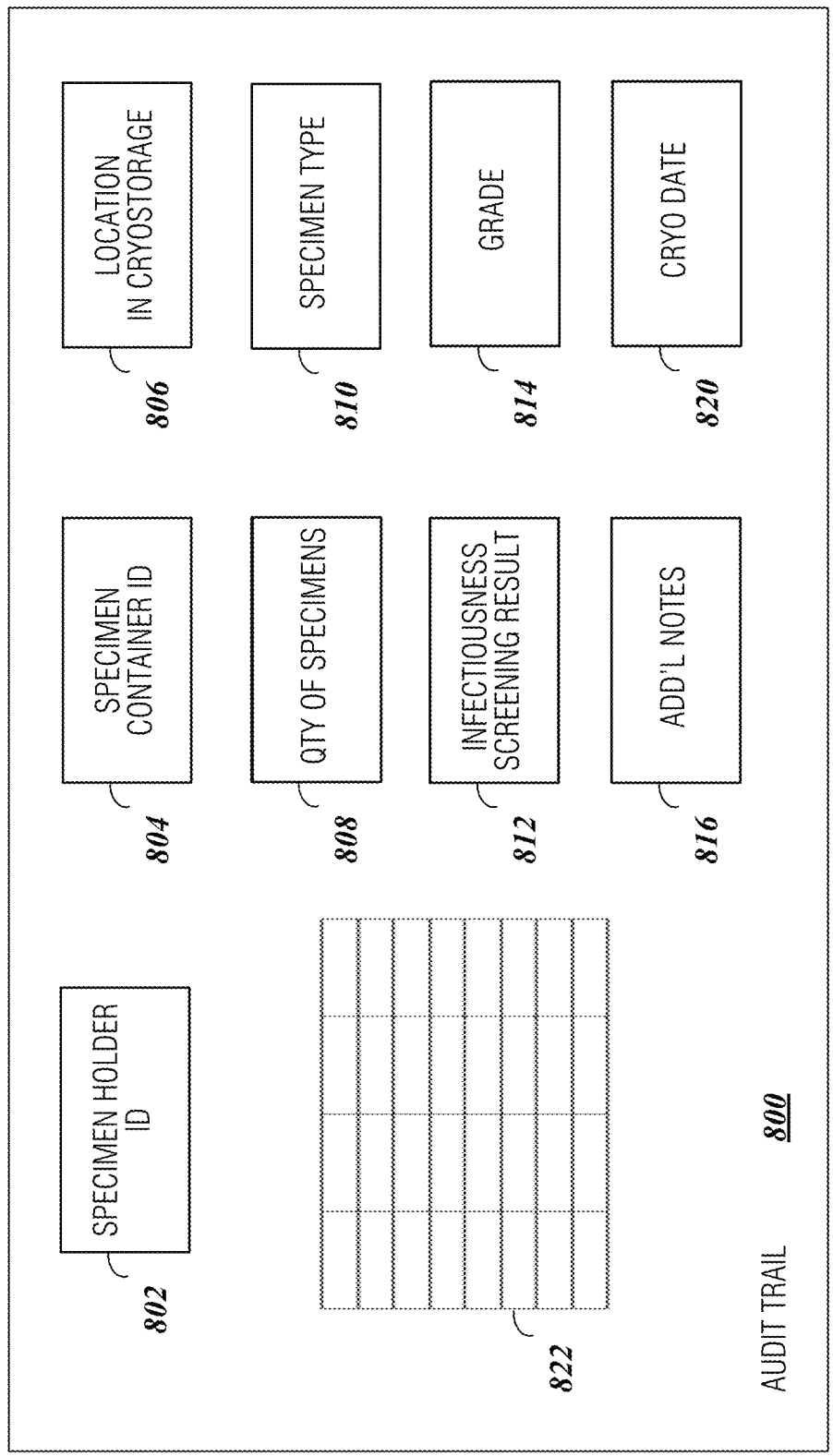
FIG. 8 is schematic diagram of an example of an audit trail record according to an embodiment.

FIG. 8 is an example of an audit trail record 800 according to an embodiment. In this example, audit trail record 800 is specific to specimen holder ID 802. Audit trail 800 may be built from a series of stored PDSs corresponding to specimen holder ID 802. In related embodiments, audit trail may be compiled through event logging. For instance, on the occurrence of PDS creation, editing of a PDS, updating of a specimen inventory, or deletion of a PDS, the following data items may be captured in a corresponding database record: date and time of the event, user ID, short description of the event type, specimen holder ID, and subject. Likewise, these data items may be captured based on events occurring in transfer system 122, such as selection of a PDS for execution, any state change of a PDS, any update of specimen location, or any update of specimen inventory. The short description of event type may be automatically selected from a closed set of predefined event types to ensure consistent wording for same types of events.

In the example as depicted in FIG. 8, besides specimen holder ID 802, record 800 additionally includes specimen container ID 804, the current location 806 in cryogenic storage (e.g., vessel, rack, shelf, cassette ID, and intra-cassette location), the quantity of specimens associated with specimen holder ID 802, the specimen type 810, screening result 812, grade 814, additional notes 816, and the cryogenic date 820. Also, log 822 is included, which shows the date and time of each event in the history of the particular specimen holder ID 802. For instance, the creation of a first PDS, printing of the label, scanning of the specimen container associated with the first PDS, opening of a work order for transfer system 122, scan of the specimen container by transfer system 122, placement of a sample holder and sample container on a cassette, placement of the cassette in the cryogenic chamber, creation of a second PDS, etc. The respective clinician involved with each action may also be identified in the log 822.

In the example of FIG. 8, the subject is not identified in the audit trail record 800. However, using the archived PDSs associated with the specimen holder and subject, the subject may easily be associated with the audit trail 800 if necessary. Otherwise, the subject's privacy may be preserved in the context of audit trail 800.

Figure 9:
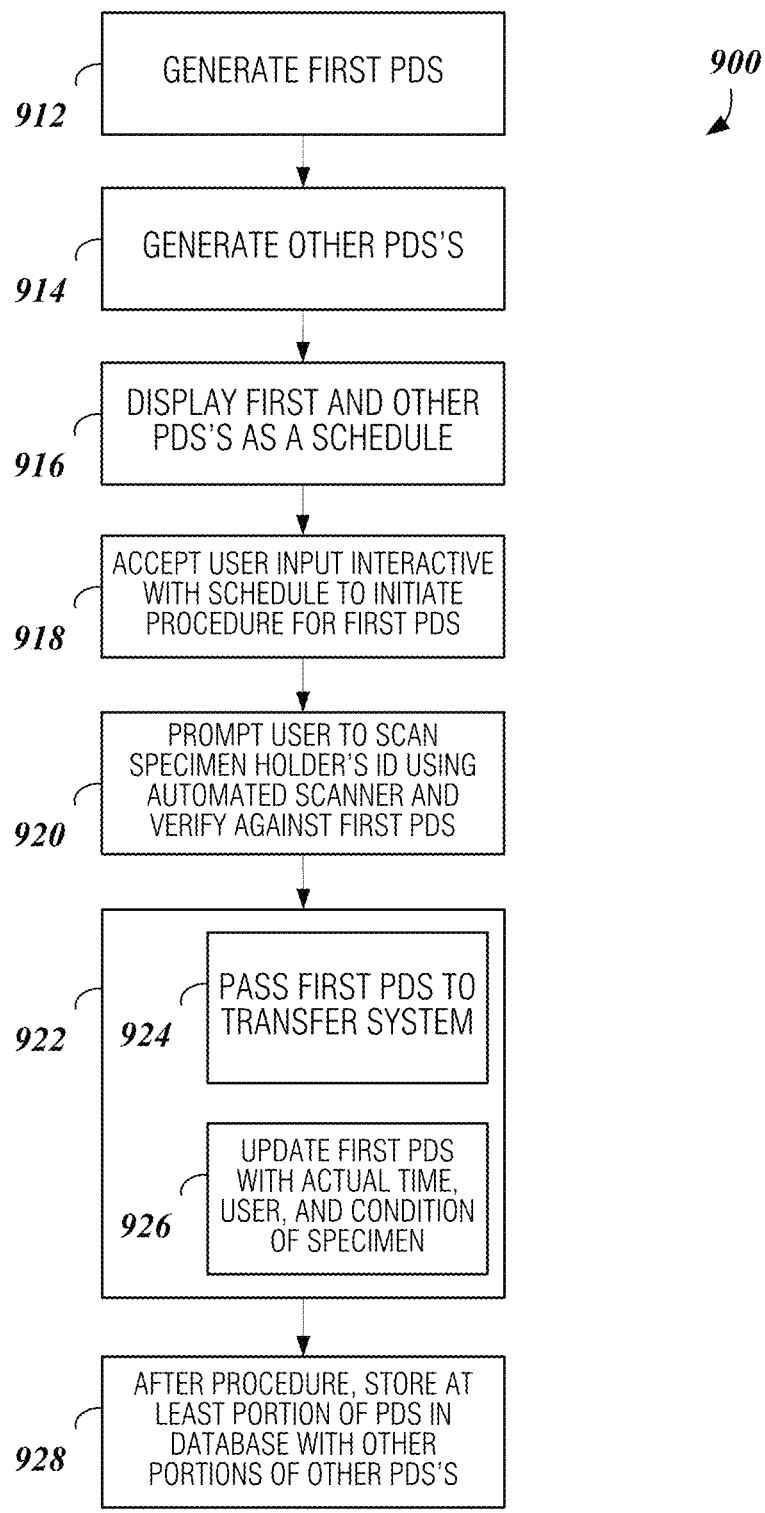
FIG. 9 is a flow diagram illustrating an example method for handling and tracking a specimen utilizing PDSs in accordance with some embodiments.

FIG. 9 shows an example method for handling and tracking a specimen utilizing PDSs in accordance with some embodiments. At 912, a first PDS is generated according to process 500 (FIG. 5), for instance. The first PDS corresponds to a certain subject, a certain procedure, and certain specimens located associated with a certain specimen holder and a certain specimen container. At 914, additional PDSs are generated for other subjects, specimens, holders, and containers. At 916, the first PDS and the other PDSs are displayed as a schedule in a GUI. The GUI supports user interaction with the schedule.

At 918, the user provides input by interacting with the GUI, which the GUI accepts. The input includes a command to initiate the procedure represented by the first PDS. At 920, the GUI prompts the user to verify the specimen holder ID using a machine-readable symbol scanner. The specimen holder's ID may be encoded in a machine-readable symbol printed on a label or printed on or inscribed in the specimen holder itself. The read specimen holder ID is compared against the specimen holder ID as stored in the first PDS.

At 922, the procedure is carried out. As part of executing the procedure, at 924, the first PDS is passed to a transfer system of the cryogenic storage system. Accordingly, the transfer system either stores, or retrieves, the specimen carrier identified by the first PDS, which in turn contains the verified sample holder (along with possibly other sample holders). At 926, the first PDS is updated to indicate the actual time of the procedure (as opposed to the scheduled time with which the first PDS was originally configured), the user carrying out the procedure, and result of the procedure, such as the location of the specimen in the cryogenic storage system in case of the procedure being a freeze procedure, or a condition of the specimen, such as a newly-assessed grade of an embryo or oocyte.

At 928, after the procedure, at least some of the information of the first PDS is stored in a database with other portions of other PDSs. For instance, an audit trail may be stored based on a log of events. In other examples, the first PDS may be archived along with other PDSs, from which records an audit trail may be generated.

FIGS. 10-18 are example implementations of a GUI implemented by PPTS 400 as it carries out operations discussed above in accordance with some embodiments. It is noted that the term "beacon" as used in FIGS. 10-18, refers to specimen containers with wireless transponders that encode unique identifiers which can be used to uniquely identify each specimen container from all other specimen containers used by a facility (e.g., clinic, storage facility). It is also noted that the term "cryodevices" as used herein and in FIGS. 10-18, refers to specimen holders that physically contact the specimens, usually in the form of straws, rods, or spatulas, and which are located in the interior of the vial of the specimen containers for storage. It is also noted that the term "cassettes" as used herein and in FIGS. 10-18, refers to structures (e.g., trays, frames) with a set of receivers (e.g., openings, apertures) sized and dimensioned to hold respective specimen holders, receivers typically arranged in a two-dimensional specimen array. It is further noted that the term "robot cassettes" as used herein and in FIGS. 10-18, refers to cassettes designed for use with a cryogenic refrigerator, which typically employs a robotic storage and retrieval mechanism (e.g., turntable, picker or elevator), and hence is denominated as a robot. In addition, the term "ticket" as used in FIGS. 10-18 refers to a PDS.

Figure 10:
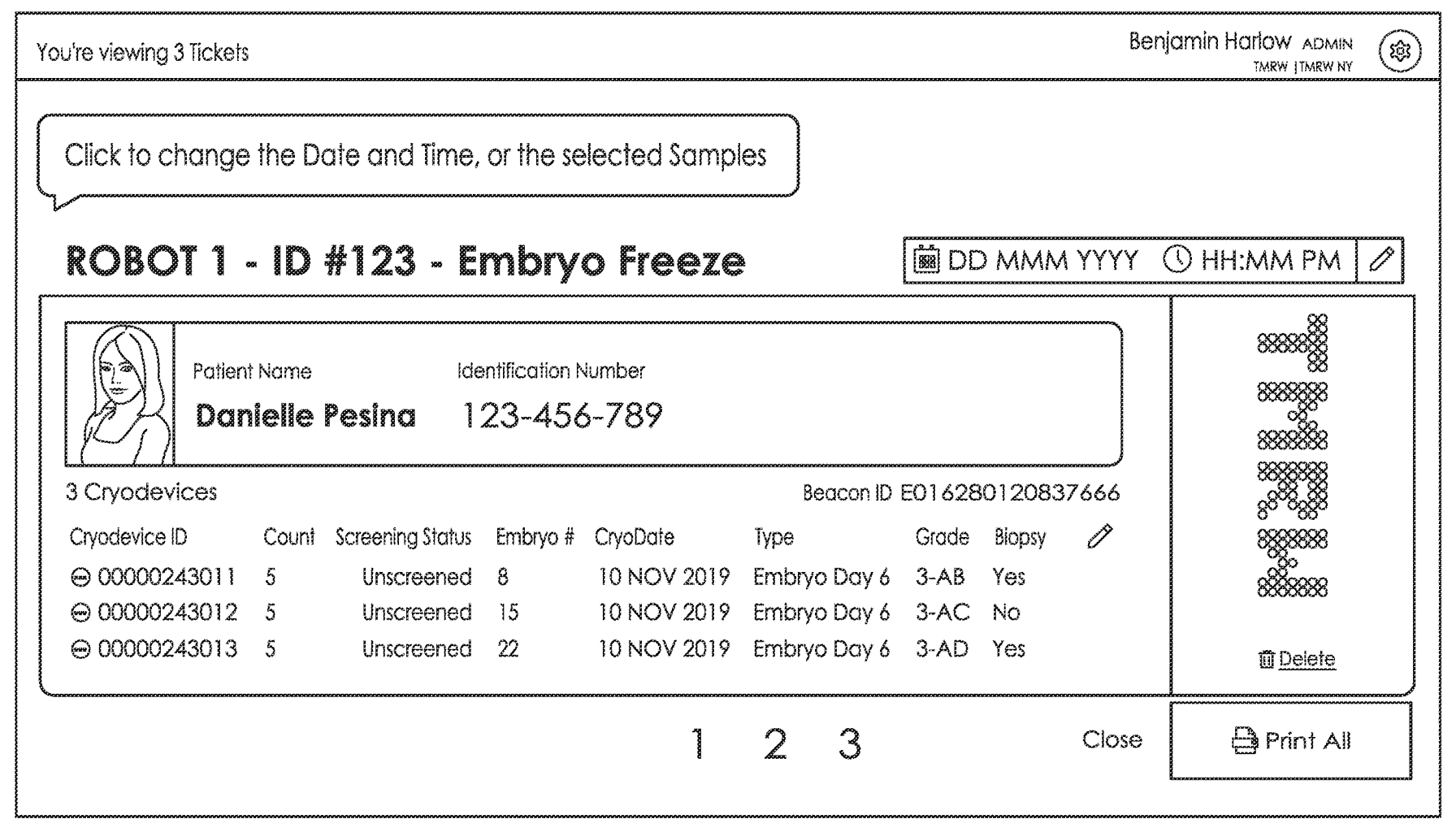
Figure 11:
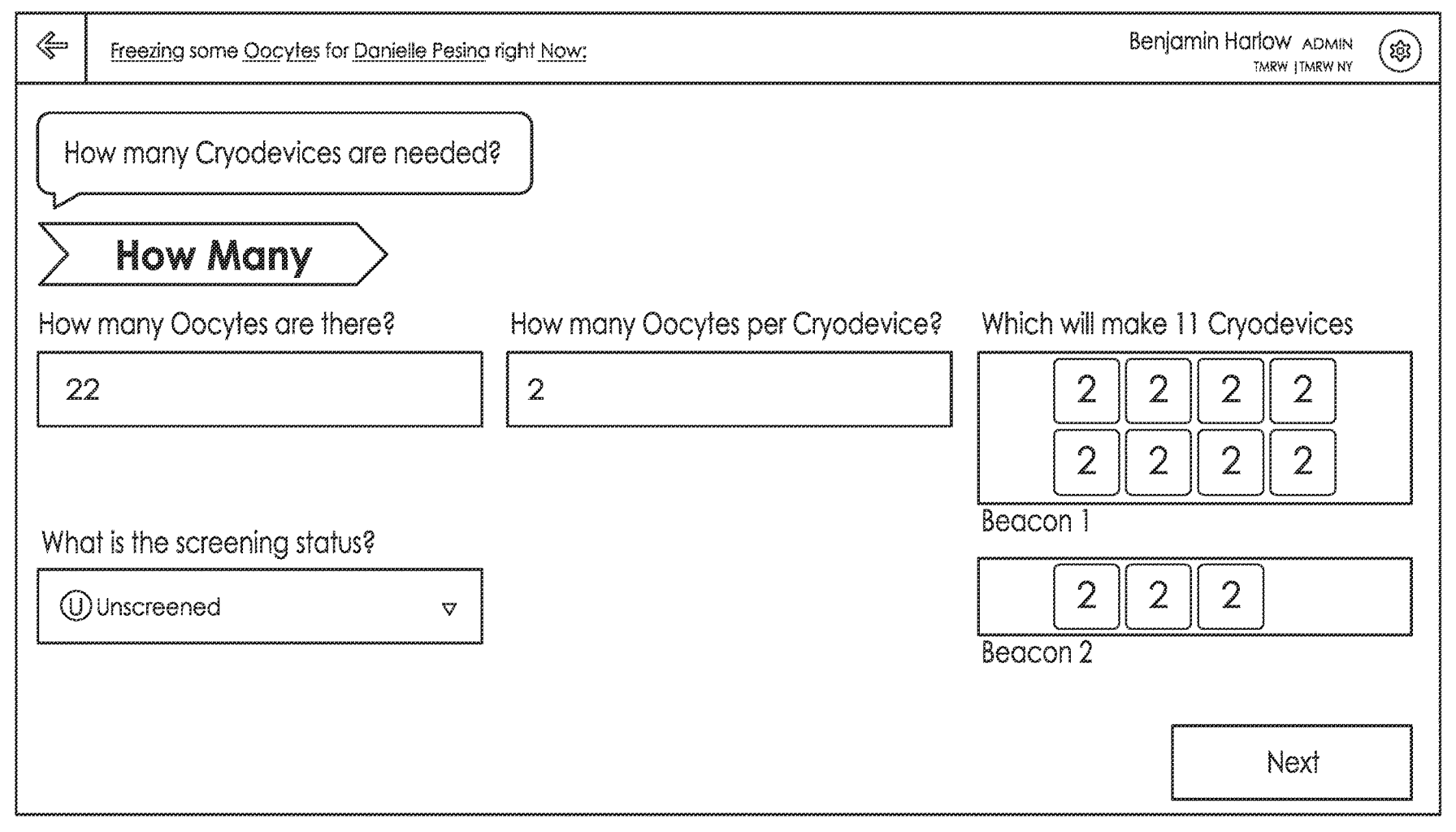

FIG. 10 is an example of a displayed PDS, or ticket, in which the beacon ID is bound to three cryodevice IDs. FIG. 11 is a displayed GUI according to one embodiment in which the PPTS assigns oocyte specimens (22 in this instance) with 2 oocytes specified per cryodevice, to two beacons. In addition, the infectiousness screening may be specified with a drop-down pick list. FIG. 12 is a displayed GUI according to one embodiment in which certain properties of oocytes may be specified by user input using drop-down pick lists for the various cryodevice IDs to select the oocyte maturity, and where respective text fields are provided to facilitate entry of notes.

Figure 13:
Figure 14:
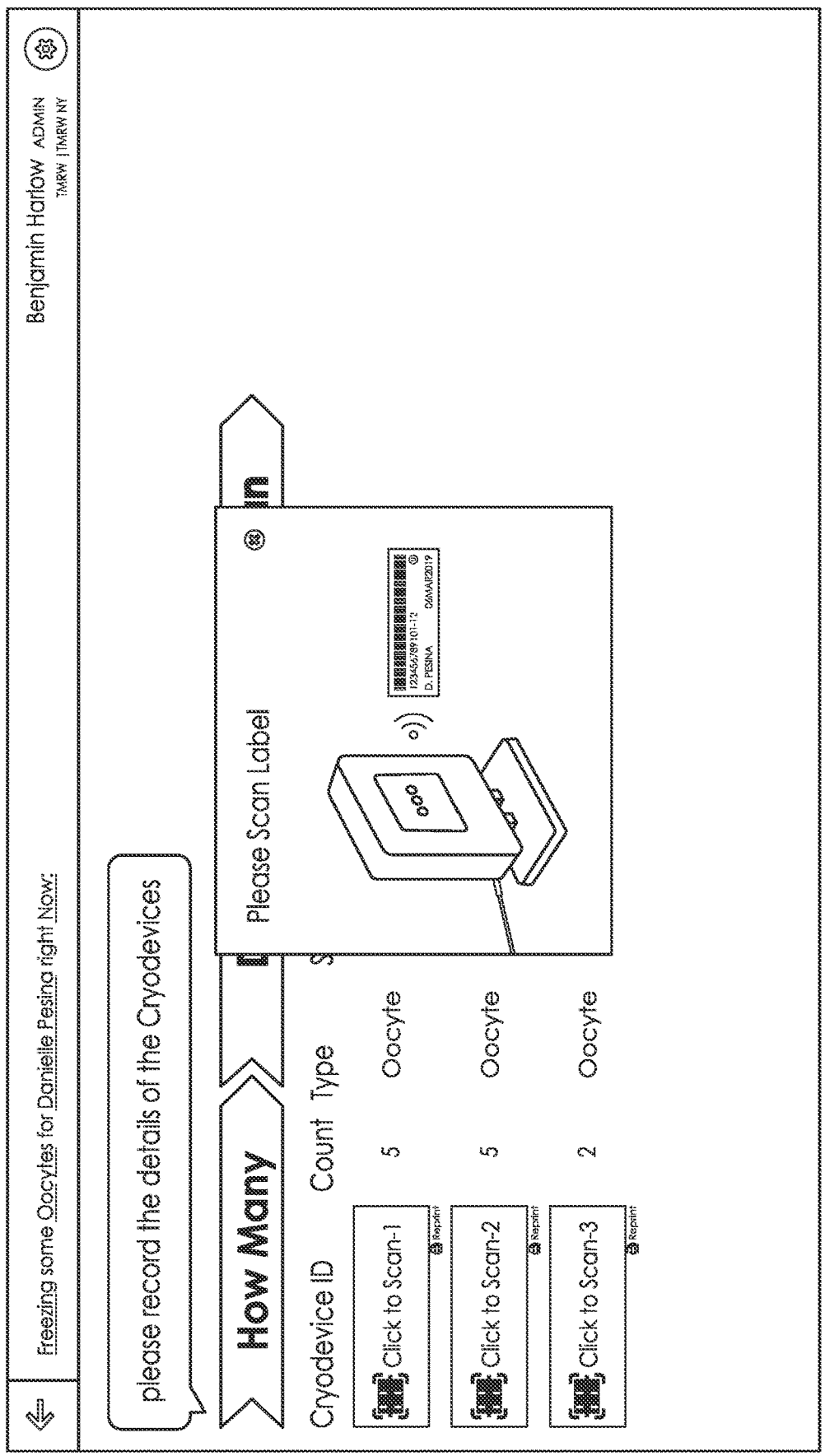

FIG. 13 is a displayed GUI according to one embodiment in which labels are generated for the cryodevices to be placed in a beacon. FIG. 14 is a displayed GUI in which printed labels are scanned to be verified according to an example embodiment. FIG. 15 is a displayed GUI according to one embodiment in which an interactive schedule of tickets is displayed. FIG. 16 is a displayed GUI in which the user is provided with interactive controls for specifying the condition or specimens belonging to a particular beacon, including specifying whether the specimen is unchanged, consumed, or discarded. Also, the user in this example may specify results of a biopsy procedure and add notes, according to an example embodiment.

FIG. 17 is a displayed GUI in which specimen inventory for a particular subject is shown according to an example embodiment. In this example, 2 active samples are indicated as being in inventory for the subject. In addition, there are two historical specimens indicated, which have been consumed in one instance, and discarded in the other. Also, one open ticket is shown for an upcoming FET procedure.

Figure 18:

FIG. 18 is a displayed GUI according to one embodiment in which status details for a particular cryodevice are shown, along with the location of the cryodevice, the beacon ID, and an audit trail of events.

Additional Notes and Examples

Example 1 is a method for handling a biological specimen of a subject for a procedure involving that specimen, the method comprising: prior to initiation of the procedure: generating a first procedure data structure (PDS) to be stored in a non-transitory machine-readable storage medium, wherein the first PDS binds (a) an identifier corresponding to the subject, (b) an indicator of a procedure to be performed on the biological specimen, wherein the first procedure includes, cryogenic storage or retrieval of the biological specimen, (c) an identifier corresponding to a specimen container of the biological specimen, (d) an identifier corresponding to a specimen holder that physically contacts the biological specimen, (e) a scheduled time for the procedure, and (f) an identifier corresponding to the first PDS; and causing a displaying, on a display device of a graphical user interface, a schedule of a plurality of PDSs including the first PDS, comprising indicia of at least a portion of bindings (a)-(f) for the first PDS; initiating the procedure associated with the first PDS based on user input interactive with the displayed schedule; following initiation of the procedure, updating the first PDS to indicate (1) an actual time of performance of the procedure, (1 is missing parent: 2) an identification of a human operator carrying out the procedure, and (1 is missing parent: 3) an indication of a condition of the biological specimen as assessed during the procedure; and following conclusion of the procedure, storing at least a portion of the first PDS, as updated, in a database in conjunction with other PDSs respectively associated with other completed procedures.

In Example 2, the subject matter of Example 1 includes, wherein generating the first PDS includes binding (a)-(f) with a total quantity of biological specimens in the specimen holder.

In Example 3, the subject matter of Examples 1-2 includes, wherein in generating the first PDS, the binding of the specimen container and the identifier corresponding to the first PDS represents a one-to-one association between the specimen container and the identifier corresponding to the PDS.

In Example 4, the subject matter of Examples 1-3 includes, wherein generating the first PDS includes binding a condition of the biological specimen with (a)-(f).

In Example 5, the subject matter of Examples 1-4 includes, wherein generating the first PDS includes: causing a graphical user interface (GUI) to prompt the user to input (i) a total quantity of specimens to be involved in the procedure, and (ii) a quantity of specimens per specimen holder; automatically determining a quantity of specimen holders to be associated with the specimen container corresponding to the first PDS based on (i) and (ii); automatically generating a set of specimen holder identifiers that includes an identifier for each specimen holder of the determined quantity of specimen holders, wherein the set of specimen holder identifiers includes (d); and binding at least a portion of the set of specimen holder identifiers with (a)-(c) and (e)-(f).

In Example 6, the subject matter of Example 5 includes, wherein when the determined quantity of specimen holder identifiers exceeds a predefined specimen holder capacity of the specimen container by an overflow amount, the method further comprises: generating a second PDS that binds (a), (b), and (e) with (g) an identifier corresponding to a second specimen container, (h) at least one identifier corresponding to one or more specimen holders of the set of specimen holder identifiers not included in the first PDS, and (j) an identifier corresponding to the second PDS.

In Example 7, the subject matter of Examples 5-6 includes, wherein generating the first PDS includes: causing a graphical user interface (GUI) to display a plurality of data-entry fields that prompt a user to enter specimen property information corresponding to each specimen holder identifier of at least a subset that includes a plurality of specimen holder identifiers from the set of specimen holder identifiers.

In Example 8, the subject matter of Examples 1-7 includes, in response to the user input, passing at least a portion of the first PDS to a controller of a cryogenic storage and retrieval system that is to store or retrieve the biological specimen.

In Example 9, the subject matter of Examples 1-8 includes, carrying out the procedure on the biological specimen and on a plurality of other biological specimens of the specimen container.

In Example 10, the subject matter of Examples 1-9 includes, wherein generating the first PDS includes further binding, with (a)-(f), an indicator of infectiousness.

In Example 11, the subject matter of Examples 1-10 includes, wherein generating the first PDS includes binding a set of properties specific to a type of the biological specimen with (a)-(f).

In Example 12, the subject matter of Example 11 includes, wherein the biological specimen is an oocyte, and the set of properties includes screening status and maturity indicia.

In Example 13, the subject matter of Examples 11-12 includes, wherein the biological specimen is an embryo, and the set of properties includes grade and biopsy status indicia.

In Example 14, the subject matter of Examples 1-13 includes, in response to generating the first PDS, producing a label to be attached to the specimen holder, the label including the identifier corresponding to the specimen holder.

In Example 15, the subject matter of Example 14 includes, wherein producing the label further includes indicating the identifier corresponding to the subject on the label.

In Example 16, the subject matter of Examples 14-15 includes, wherein producing the label further includes indicating a machine-readable symbol corresponding to the identifier corresponding to the specimen holder.

In Example 17, the subject matter of Examples 1-16 includes, following initiation of the procedure: causing an automated symbol reader to read a machine-readable symbol affixed to the specimen holder; and verifying the read symbol against the identifier corresponding to the specimen holder and, in response to a result of the verifying, displaying a notification for viewing by the human operator, the notification being indicative of authorization to proceed with carrying out the procedure.

In Example 18, the subject matter of Examples 1-17 includes, wherein storing said at least portion of the first PDS, as updated, in the database includes storing the entire updated first PDS as a record in the database.

In Example 19, the subject matter of Examples 1-18 includes, wherein storing said at least portion of the first PDS, as updated, in the database includes logging events based on activities represented by the first PDS as an event log data structure.

In Example 20, the subject matter of Examples 1-19 includes, wherein storing said at least portion of the first PDS, as updated, in the database includes generating an audit-trail record based on the first PDS.

Example 21 is at least one non-transitory machine-readable storage medium comprising instructions that, when executed by a processor-based computing system, cause the computing system to implement a process for handling a biological specimen of a subject for a procedure involving that specimen, wherein: prior to initiation of the procedure: a first procedure data structure (PDS) to be stored in a non-transitory machine-readable storage medium is generated, wherein the first PDS binds (a) an identifier corresponding to the subject, (b) an indicator of a procedure to be performed on the biological specimen, wherein the first procedure includes, cryogenic storage or retrieval of the biological specimen, (c) an identifier corresponding to a specimen container of the biological specimen, (d) an identifier corresponding to a specimen holder that physically contacts the biological specimen, (e) a scheduled time for the procedure, and (f) an identifier corresponding to the first PDS; and a schedule of a plurality of PDSs including the first PDS, is caused to be displayed on a display device of a graphical user interface, wherein the schedule includes indicia of at least a portion of bindings (a)-(f) for the first PDS; the procedure associated with the first PDS is initiated based on user input interactive with the displayed schedule; following initiation of the procedure, the first PDS is updated based on user input to indicate (1) an actual time of performance of the procedure, (2) an identification of a human operator carrying out the procedure, and (3) an indication of a condition of the biological specimen as assessed during the procedure; and following conclusion of the procedure, at least a portion of the first PDS, as updated, is stored in a database in conjunction with other PDSs respectively associated with other completed procedures.

In Example 22, the subject matter of Example 21 includes, wherein the PDS indicates a total quantity of biological specimens in the specimen holder.

In Example 23, the subject matter of Examples 21-22 includes, wherein the binding of the specimen container and the identifier corresponding to the PDS represents a one-to-one association between the specimen container and the identifier corresponding to the PDS.

In Example 24, the subject matter of Examples 21-23 includes, wherein the PDS indicates a condition of the biological specimen.

In Example 25, the subject matter of Example 24 includes, instructions that, when executed by the computing system, cause the computing system to: initiate prompting of the user to input, via graphical user interface (GUI), (i) a total quantity of specimens to be involved in the procedure, and (ii) a quantity of specimens per specimen holder; determine a quantity of specimen holders to be associated with the specimen container corresponding to the first PDS based on (i) and (ii); generate a set of specimen holder identifiers that includes an identifier for each specimen holder of the determined quantity of specimen holders, wherein the set of specimen holder identifiers includes (d); and bind at least a portion of the set of specimen holder identifiers with (a)-(c) and (e)-(f).

In Example 26, the subject matter of Example 25 includes, wherein when the determined quantity of specimen holder identifiers exceeds a predefined specimen holder capacity of the specimen container by an overflow amount: a second PDS is generated that binds (a), (b), and (e) with (g) an identifier corresponding to a second specimen container, (h) at least one identifier corresponding to one or more specimen holders of the set of specimen holder identifiers not included in the first PDS, and (j) an identifier corresponding to the second PDS.

In Example 27, the subject matter of Examples 25-26 includes, instructions that, when executed by the computing system, cause the computing system to: cause the GUI to display a plurality of data-entry fields that prompt a user to enter specimen property information corresponding to each specimen holder identifier of at least a subset that includes a plurality of specimen holder identifiers from the set of specimen holder identifiers.

In Example 28, the subject matter of Examples 21-27 includes, instructions that, when executed by the computing system, cause the computing system to: in response to the user input, pass at least a portion of the first PDS to a controller of a cryogenic storage and retrieval system that is to store or retrieve the biological specimen.

In Example 29, the subject matter of Examples 21-28 includes, instructions that, when executed by the computing system, cause the computing system to: carry out the procedure on the biological specimen and on a plurality of other biological specimens of the specimen container.

In Example 30, the subject matter of Examples 21-29 includes, wherein the first PDS further binds, with (a)-(f), an indicator of infectiousness.

In Example 31, the subject matter of Examples 21-30 includes, wherein the first PDS further binds, with (a)-(f), a set of properties specific to a type of the biological specimen.

In Example 32, the subject matter of Example 31 includes, wherein the biological specimen is an oocyte, and the set of properties includes screening status and maturity indicia.

In Example 33, the subject matter of Examples 31-32 includes, wherein the biological specimen is an embryo, and the set of properties includes grade and biopsy status indicia.

In Example 34, the subject matter of Examples 21-33 includes, instructions that, when executed by the computing system, cause the computing system to: in response to generating the first PDS, produce a label to be attached to the specimen holder, the label including the identifier corresponding to the specimen holder.

In Example 35, the subject matter of Example 34 includes, wherein the label further includes the identifier corresponding to the subject.

In Example 36, the subject matter of Examples 34-35 includes, wherein the label further includes a machine-readable symbol corresponding to the identifier corresponding to the specimen holder.

In Example 37, the subject matter of Examples 21-36 includes, instructions that, when executed by the computing system, cause the computing system to: following initiation of the procedure: cause an automated symbol reader to read a machine-readable symbol affixed to the specimen holder; and verify the read symbol against the identifier corresponding to the specimen holder and, in response to a result of the verifying, displaying a notification for viewing by the human operator, the notification being indicative of authorization to proceed with carrying out the procedure.

In Example 38, the subject matter of Examples 21-37 includes, wherein storing said at least portion of the first PDS, as updated, in the database includes storing the entire updated first PDS as a record in the database.

In Example 39, the subject matter of Examples 21-38 includes, wherein storing said at least portion of the first PDS, as updated, in the database includes logging events based on activities represented by the first PDS as an event log data structure.

In Example 40, the subject matter of Examples 21-39 includes, wherein storing said at least portion of the first PDS, as updated, in the database includes generating an audit-trail record based on the first PDS.

Example 41 is an apparatus for facilitating handling of a biological specimen of a subject for a procedure involving that specimen, the apparatus comprising: a processor-based computing system, including a storage device, input/output devices, and processing circuitry; instructions executable by the processor-based computing system stored in the storage device, wherein the instructions, when executed, cause the computing system to: prior to initiation of the procedure: generate a first procedure data structure (PDS) to be stored in a non-transitory machine-readable storage medium, wherein the first PDS binds (a) an identifier corresponding to the subject, (b) an indicator of a procedure to be performed on the biological specimen, wherein the first procedure includes, cryogenic storage or retrieval of the biological specimen, (c) an identifier corresponding to a specimen container of the biological specimen, (d) an identifier corresponding to a specimen holder that physically contacts the biological specimen, (e) a scheduled time for the procedure, and (f) an identifier corresponding to the first PDS; and cause a schedule of a plurality of PDSs including the first PDS, to be displayed on a display device of a graphical user interface, wherein the schedule includes indicia of at least a portion of bindings (a)-(f) for the first PDS; initiate the procedure associated with the first PDS based on user input interactive with the displayed schedule; following initiation of the procedure, update the first PDS based on user input to indicate (1) an actual time of performance of the procedure, (2) an identification of a human operator carrying out the procedure, and (3) an indication of a condition of the biological specimen as assessed during the procedure; and following conclusion of the procedure, store at least a portion of the first PDS, as updated, in a database in conjunction with other PDSs respectively associated with other completed procedures.

In Example 42, the subject matter of Example 41 includes, wherein the PDS indicates a total quantity of biological specimens in the specimen holder.

In Example 43, the subject matter of Examples 41-42 includes, wherein the binding of the specimen container and the identifier corresponding to the PDS represents a one-to-one association between the specimen container and the identifier corresponding to the PDS.

In Example 44, the subject matter of Examples 41-43 includes, wherein the PDS indicates a condition of the biological specimen.

In Example 45, the subject matter of Examples 41-44 includes, instructions that, when executed by the computing system, cause the computing system to: initiate prompting of the user to input, via graphical user interface (GUI), (i) a total quantity of specimens to be involved in the procedure, and (ii) a quantity of specimens per specimen holder; determine a quantity of specimen holders to be associated with the specimen container corresponding to the first PDS based on (i) and (ii); generate a set of specimen holder identifiers that includes an identifier for each specimen holder of the determined quantity of specimen holders, wherein the set of specimen holder identifiers includes (d); and bind at least a portion of the set of specimen holder identifiers with (a)-(c) and (e)-(f).

In Example 46, the subject matter of Example 45 includes, wherein when the determined quantity of specimen holder identifiers exceeds a predefined specimen holder capacity of the specimen container by an overflow amount: a second PDS is generated that binds (a), (b), and (e) with (g) an identifier corresponding to a second specimen container, (h) at least one identifier corresponding to one or more specimen holders of the set of specimen holder identifiers not included in the first PDS, and (j) an identifier corresponding to the second PDS.

In Example 47, the subject matter of Examples 45-46 includes, instructions that, when executed by the computing system, cause the computing system to: cause the GUI to display a plurality of data-entry fields that prompt a user to enter specimen property information corresponding to each specimen holder identifier of at least a subset that includes a plurality of specimen holder identifiers from the set of specimen holder identifiers.

In Example 48, the subject matter of Examples 41-47 includes, instructions that, when executed by the computing system, cause the computing system to: in response to the user input, pass at least a portion of the first PDS to a controller of a cryogenic storage and retrieval system that is to store or retrieve the biological specimen.

In Example 49, the subject matter of Examples 41-48 includes, instructions that, when executed by the computing system, cause the computing system to: carry out the procedure on the biological specimen and on a plurality of other biological specimens of the specimen container.

In Example 50, the subject matter of Examples 41-49 includes, wherein the first PDS further binds, with (a)-(f), an indicator of infectiousness.

In Example 51, the subject matter of Examples 41-50 includes, wherein the first PDS further binds, with (a)-(f), a set of properties specific to a type of the biological specimen.

In Example 52, the subject matter of Example 51 includes, wherein the biological specimen is an oocyte, and the set of properties includes screening status and maturity indicia.

In Example 53, the subject matter of Examples 51-52 includes, wherein the biological specimen is an embryo, and the set of properties includes grade and biopsy status indicia.

In Example 54, the subject matter of Examples 41-53 includes, instructions that, when executed by the computing system, cause the computing system to: in response to generating the first PDS, produce a label to be attached to the specimen holder, the label including the identifier corresponding to the specimen holder.

In Example 55, the subject matter of Example 54 includes, wherein the label further includes the identifier corresponding to the subject.

In Example 56, the subject matter of Examples 54-55 includes, wherein the label further includes a machine-readable symbol corresponding to the identifier corresponding to the specimen holder.

In Example 57, the subject matter of Examples 41-56 includes, instructions that, when executed by the computing system, cause the computing system to: following initiation of the procedure: cause an automated symbol reader to read a machine-readable symbol affixed to the specimen holder; and verify the read symbol against the identifier corresponding to the specimen holder and, in response to a result of the verifying, displaying a notification for viewing by the human operator, the notification being indicative of authorization to proceed with carrying out the procedure.

In Example 58, the subject matter of Examples 41-57 includes, wherein storing said at least portion of the first PDS, as updated, in the database includes storing the entire updated first PDS as a record in the database.

In Example 59, the subject matter of Examples 41-58 includes, wherein storing said at least portion of the first PDS, as updated, in the database includes logging events based on activities represented by the first PDS as an event log data structure.

In Example 60, the subject matter of Examples 41-59 includes, wherein storing said at least portion of the first PDS, as updated, in the database includes generating an audit-trail record based on the first PDS.

Example 61 is a system comprising means to implement of any of Examples 1-60.

The various implementations and embodiments described above can be combined to provide further implementations and embodiments. All of the commonly assigned US patent application publications, US patent applications, foreign patents, and foreign patent applications referred to in this specification or listed in the Application Data Sheet, including but not limited U.S. patent application 62/900,281, filed Sep. 13, 2019; U.S. patent application 62/880,786, filed Jul. 31, 2019; U.S. patent application 62/879,160, filed Jul. 26, 2019; U.S. patent application 62/741,986, filed Oct. 5, 2018; and U.S. patent application 62/741,998, filed Oct. 5, 2018, are each incorporated herein by reference, in their entirety. These and other changes can be made to the embodiments in light of the above-detailed description.

In general, in the following claims, the terms used should not be construed to limit the claims to the specific implementations and embodiments disclosed in the specification and the claims, but should be construed to include all possible implementations and embodiments along with the full scope of equivalents to which such claims are entitled. Accordingly, the claims are not limited by the disclosure.

The invention claimed is:

1. A method for handling a biological specimen of a subject for a procedure involving that specimen, the method comprising:

prior to initiation of the procedure, generating, by a data-processing system operating under program control, a first procedure data structure (PDS) to be stored in a non-transitory machine-readable storage medium, wherein the first PDS is a single data structure that uniquely binds (a) an identifier corresponding to the subject, (b) an indicator of a procedure to be performed on the biological specimen, wherein the procedure includes cryogenic storage or retrieval of the biological specimen, (c) an identifier corresponding to a specimen container of the biological specimen, (d) an identifier corresponding to a specimen holder that physically contacts the biological specimen, (e) a scheduled time for the procedure, and (f) an identifier corresponding to the first PDS;

initiating, by the data-processing system operating under program control, the procedure associated with the first PDS based on user input interactive with the displayed schedule;

in response to initiation of the procedure, causing, by the data-processing system operating under program control, a cryogenic storage and retrieval system to autonomously retrieve, from cryogenic storage, the biological specimen according to at least a portion of the first PDS as part of carrying out the procedure;

following initiation of the procedure, updating the first PDS, by the data-processing system operating under program control, to indicate (1) an actual time of performance of the procedure, (2) an identification of a human operator carrying out the procedure, and (3) an indication of a condition of the biological specimen as assessed during the procedure; and following conclusion of the procedure, storing, by the data-processing system operating under program control, at least a portion of the first PDS, as updated, in a database in conjunction with other PDSs respectively associated with other completed procedures.

2. The method of claim 1, wherein generating the first PDS includes binding (a)-(f) with a total quantity of biological specimens in the specimen holder, a condition of the biological specimen, a set of properties specific to a type of the biological specimen, and an indicator of infectiousness of the biological specimen.

3. The method of claim 2, wherein when the biological specimen is an oocyte, the set of properties includes screening status and maturity indicia, and when the biological specimen is an embryo, the set of properties includes grade and biopsy status indicia.

4. The method of claim 1, wherein generating the first PDS includes:

causing, by the data-processing system operating under program control, a graphical user interface (GUI) to prompt the user to input (i) a total quantity of specimens to be involved in the procedure, and (ii) a quantity of specimens per specimen holder;

determining, by the data-processing system operating under program control, a quantity of specimen holders to be associated with the specimen container corresponding to the first PDS based on (i) and (ii);

generating, by the data-processing system operating under program control, a set of specimen holder identifiers that includes an identifier for each specimen holder of the determined quantity of specimen holders, wherein the set of specimen holder identifiers includes (d); and binding, by the data-processing system operating under program control, at least a portion of the set of specimen holder identifiers with (a)-(c) and (e)-(f).

5. The method of claim 4, wherein when the determined quantity of specimen holder identifiers exceeds a predefined specimen holder capacity of the specimen container by an overflow amount, the method further comprises:

generating, by the data-processing system operating under program control, a second PDS that binds (a), (b), and (e) with (g) an identifier corresponding to a second specimen container, (h) at least one identifier corresponding to one or more specimen holders of the set of specimen holder identifiers not included in the first PDS, and (j) an identifier corresponding to the second PDS.

6. The method of claim 1, further comprising:

carrying out the procedure on the biological specimen and on a plurality of other biological specimens of the specimen container based on the first PDS.

7. The method of claim 1, further comprising:

following initiation of the procedure:
causing, by the data-processing system operating under program control, an automated symbol reader to read a machine-readable symbol affixed to the specimen holder; and
verifying, by the data-processing system operating under program control, the read symbol against the identifier corresponding to the specimen holder and, in response to a result of the verifying, displaying a notification for viewing by the human operator, the notification being indicative of authorization to proceed with carrying out the procedure.

8. At least one non-transitory machine-readable storage medium comprising instructions that, when executed by a processor-based computing system, cause the computing system to implement a process for handling a biological specimen of a subject for a procedure involving that specimen, wherein:

prior to initiation of the procedure, a first procedure data structure (PDS) to be stored in a non-transitory machine-readable storage medium is generated, wherein the first PDS is a single data structure that uniquely binds (a) an identifier corresponding to the subject, (b) an indicator of a procedure to be performed on the biological specimen, wherein the procedure includes cryogenic storage or retrieval of the biological specimen, (c) an identifier corresponding to a specimen container of the biological specimen, (d) an identifier corresponding to a specimen holder that physically contacts the biological specimen, (e) a scheduled time for the procedure, and (f) an identifier corresponding to the first PDS;

the procedure associated with the first PDS is initiated based on user input interactive with the displayed schedule;

in response to initiation of the procedure, a cryogenic storage and retrieval system autonomously retrieves the biological specimen from cryogenic storage according to at least a portion of the first PDS as part of carrying out the procedure;

following initiation of the procedure, the first PDS is updated based on user input to indicate (1) an actual time of performance of the procedure, (2) an identification of a human operator carrying out the procedure, and (3) an indication of a condition of the biological specimen as assessed during the procedure; and following conclusion of the procedure, at least a portion of the first PDS, as updated, is stored in a database in conjunction with other PDSs respectively associated with other completed procedures.

9. The at least one non-transitory machine-readable storage medium of claim 8, wherein the binding of the specimen container and the identifier corresponding to the PDS represents a one-to-one association between the specimen container and the identifier corresponding to the PDS.

10. The at least one non-transitory machine-readable storage medium of claim 8, further comprising instructions that, when executed by the computing system, cause the computing system to:

initiate prompting of the user to input, via a graphical user interface (GUI), (i) a total quantity of specimens to be involved in the procedure, and (ii) a quantity of specimens per specimen holder;

determine a quantity of specimen holders to be associated with the specimen container corresponding to the first PDS based on (i) and (ii);

generate a set of specimen holder identifiers that includes an identifier for each specimen holder of the determined quantity of specimen holders, wherein the set of specimen holder identifiers includes (d); and bind at least a portion of the set of specimen holder identifiers with (a)-(c) and (e)-(f); and when the determined quantity of specimen holder identifiers exceeds a predefined specimen holder capacity of the specimen container by an overflow amount, a second PDS is generated that binds (a), (b), and (e) with (g) an identifier corresponding to a second specimen container, (h) at least one identifier corresponding to one or more specimen holders of the set of specimen holder identifiers not included in the first PDS, and (j) an identifier corresponding to the second PDS.

11. The at least one non-transitory machine-readable storage medium of claim 10, further comprising instructions that, when executed by the computing system, cause the computing system to:

cause the GUI to display a plurality of data-entry fields that prompt a user to enter specimen property information corresponding to each specimen holder identifier of at least a subset that includes a plurality of specimen holder identifiers from the set of specimen holder identifiers.

12. The at least one non-transitory machine-readable storage medium of claim 8, wherein the first PDS further binds, with (a)-(f), a condition of the biological specimen, an indicator of infectiousness of the biological specimen, and a set of properties specific to a type of the biological specimen.

13. The at least one non-transitory machine-readable storage medium of claim 8, further comprising instructions that, when executed by the computing system, cause the computing system to:

following initiation of the procedure:
cause an automated symbol reader to read a machine-readable symbol affixed to the specimen holder; and
verify the read symbol against the identifier corresponding to the specimen holder and, in response to a result of the verifying, displaying a notification for viewing by the human operator, the notification being indicative of authorization to proceed with carrying out the procedure.

14. The at least one non-transitory machine-readable storage medium of claim 8, wherein the instructions that, when executed by the computing system, cause the computing system to store at least a portion of the first PDS, as updated, in the database, cause the computing system to store the entire updated first PDS as a record in the database.

15. The at least one non-transitory machine-readable storage medium of claim 8, wherein the instructions that, when executed by the computing system, cause the computing system to store at least a portion of the first PDS, as updated, in the database, cause the computing system to generate an audit-trail record based on the first PDS.

16. An apparatus for facilitating handling of a biological specimen of a subject for a procedure involving that specimen, the apparatus comprising:
a processor-based computing system, including a storage device, input/output devices, and processing circuitry;
instructions executable by the processor-based computing system stored in the storage device, wherein the instructions, when executed, cause the computing system to: prior to initiation of the procedure, generate a first procedure data structure (PDS) to be stored in a non-transitory machine-readable storage medium, wherein the first PDS is a single data structure that uniquely binds (a) an identifier corresponding to the subject, (b) an indicator of a procedure to be performed on the biological specimen, wherein the procedure includes cryogenic storage or retrieval of the biological specimen, (c) an identifier corresponding to a specimen container of the biological specimen, (d) an identifier corresponding to a specimen holder that physically contacts the biological specimen, (e) a scheduled time for the procedure, and (f) an identifier corresponding to the first PDS;
initiate the procedure associated with the first PDS based on user input interactive with the displayed schedule;
in response to initiation of the procedure, cause a cryogenic storage and retrieval system to autonomously retrieve, from cryogenic storage, the biological specimen according to at least a portion of the first PDS as part of carrying out the procedure;
following initiation of the procedure, update the first PDS based on user input to indicate (1) an actual time of performance of the procedure, (2) an identification of a human operator carrying out the procedure, and (3) an indication of a condition of the biological specimen as assessed during the procedure; and
following conclusion of the procedure, store at least a portion of the first PDS, as updated, in a database in conjunction with other PDSs respectively associated with other completed procedures.

17. The apparatus of claim 16, wherein the PDS indicates a total quantity of biological specimens in the specimen holder.

18. The apparatus of claim 16, wherein the binding of the specimen container and the identifier corresponding to the PDS represents a one-to-one association between the specimen container and the identifier corresponding to the PDS.

19. The apparatus of claim 16, further comprising instructions that, when executed by the computing system, cause the computing system to:
initiate prompting of the user to input, via a graphical user interface (GUI), (i) a total quantity of specimens to be involved in the procedure, and (ii) a quantity of specimens per specimen holder;
determine a quantity of specimen holders to be associated with the specimen container corresponding to the first PDS based on (i) and (ii);
generate a set of specimen holder identifiers that includes an identifier for each specimen holder of the determined quantity of specimen holders, wherein the set of specimen holder identifiers includes (d); and
bind at least a portion of the set of specimen holder identifiers with (a)-(c) and (e)-(f).

20. The apparatus of claim 19, wherein when the determined quantity of specimen holder identifiers exceeds a predefined specimen holder capacity of the specimen container by an overflow amount:
a second PDS is generated that binds (a), (b), and (e) with (g) an identifier corresponding to a second specimen container, (h) at least one identifier corresponding to one or more specimen holders of the set of specimen holder identifiers not included in the first PDS, and (j) an identifier corresponding to the second PDS.

21. The apparatus of claim 19, wherein the instructions that, when executed by the computing system, cause the computing system to store at least a portion of the first PDS, as updated, in the database, cause the computing system to store the entire updated first PDS as a record in the database.

22. The apparatus of claim 19, wherein the instructions that, when executed by the computing system, cause the computing system to store at least a portion of the first PDS, as updated, in the database, cause the computing system to log events based on activities represented by the first PDS as an event log data structure.

23. The apparatus of claim 16, further comprising instructions that, when executed by the computing system, cause the computing system to:
carry out the procedure on the biological specimen and on a plurality of other biological specimens of the specimen container.

24. The apparatus of claim 16, wherein the first PDS further binds, with (a)-(f), a set of properties specific to a type of the biological specimen, and wherein when the biological specimen is an oocyte, the set of properties includes screening status and maturity indicia, and when the biological specimen is an embryo, the set of properties includes grade and biopsy status indicia.

25. The apparatus of claim 16, further comprising instructions that, when executed by the computing system, cause the computing system to:
in response to generating the first PDS, produce a label to be attached to the specimen holder, the label including a machine-readable symbol corresponding to an identifier that corresponds with the specimen holder.

26. The apparatus of claim 16, further comprising instructions that, when executed by the computing system, cause the computing system to:
following initiation of the procedure:
cause an automated symbol reader to read a machine-readable symbol affixed to the specimen holder; and
verify the read symbol against the identifier corresponding to the specimen holder and, in response to a result of the verifying, displaying a notification for viewing by the human operator, the notification being indicative of authorization to proceed with carrying out the procedure.

* * * * *